US009439982B2

(12) United States Patent
Guminski et al.

(10) Patent No.: US 9,439,982 B2
(45) Date of Patent: Sep. 13, 2016

(54) FLUORESCENT CYANINE-POLYAMINE DERIVATIVES AS A DIAGNOSTIC PROBE

(75) Inventors: Yves Guminski, Lagarrigue (FR); Thierry Imbert, Viviers Les Montagnes (FR); Sabrina Pesnel, Olivet (FR); Arnaud Pillon, Saint Orens de Gameville (FR); Alain Le Pape, Lignieres De Touraine (FR); Stephanie Lerondel, Orleans (FR)

(73) Assignees: PIERRE FABRE MEDICAMENT, Boulogne-Billancourt (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 61 days.

(21) Appl. No.: 13/822,535

(22) PCT Filed: Nov. 24, 2011

(86) PCT No.: PCT/EP2011/070980
§ 371 (c)(1),
(2), (4) Date: Mar. 12, 2013

(87) PCT Pub. No.: WO2012/069607
PCT Pub. Date: May 31, 2012

(65) Prior Publication Data
US 2013/0183247 A1 Jul. 18, 2013

(30) Foreign Application Priority Data
Nov. 24, 2010 (FR) ...................................... 10 59687

(51) Int. Cl.
| A61B 5/00 | (2006.01) |
| A61B 8/00 | (2006.01) |
| A61B 10/00 | (2006.01) |
| A61K 49/00 | (2006.01) |
| C07D 209/14 | (2006.01) |
| C07D 403/06 | (2006.01) |

(52) U.S. Cl.
CPC ......... *A61K 49/0032* (2013.01); *C07D 209/14* (2013.01); *C07D 403/06* (2013.01); *A61K 49/0017* (2013.01)

(58) Field of Classification Search
USPC ......................................................... 424/9.6
See application file for complete search history.

(56) References Cited

U.S. PATENT DOCUMENTS

| 5,968,479 A * | 10/1999 | Ito et al. ........................ 424/9.6 |
| 2005/0214833 A1* | 9/2005 | Carter et al. ...................... 435/6 |
| 2007/0148094 A1* | 6/2007 | Uzgiris et al. ................ 424/9.34 |
| 2012/0252059 A1 | 10/2012 | Annereau et al. |

FOREIGN PATENT DOCUMENTS

| WO | WO 99/03823 A2 | 1/1999 |
| WO | WO 2005/100363 A1 | 10/2005 |
| WO | WO 2009/013360 A1 | 1/2009 |
| WO | WO 2009/078970 A1 | 6/2009 |

OTHER PUBLICATIONS

Kovalska et al. (J. Biochem. Biophys. Methods 2006, 68, 155-165).*
Barret et al., "F14512. a Potent Antitumor Agent Targeting Topoisomerase II Vectored into Cancer Cells via the Polyamine Transport System", Cancer Res 2008, Dec. 1, 2008, vol. 68, No. 23, pp. 9845-9853.
Blagbrough et al., "Practical Synthesis of Unsymmetrical Polyamine Amides", Tetrahedron Letters, 1998, vol. 39, pp. 439-442.
Bouteiller et al., "Novel Water-Soluble Near-Infrafred Cyanine Dyes: Synthesis, Spectral Properties and Use in the Preparation of Internally Quenched Fluorescent Probes", Bioconjugate Chem., 2007, vol. 18, No. 4, pp. 1303-1317.
Chen et al., "In vivo Near-Infrared Fluorescence Imaging of Integrin ov63 in Brain Tumor Xenografts", Cancer Research, Nov. 1, 2004, vol. 64, pp. 8009-8014.
Cheng et al., "Near-infrared Fluorescent Deoxyglucose Analog for Tumor Optical imaging in Cell Culture and in Living Mice", Bioconjug Chem., 2006, vol. 17, No. 3, pp. 662-669 (NIH Public Access Author Manuscript, 18 pages).
Fu et al., "Quantification of polyamines in human erythrocytes using a new near-infrared cyanine 1-(εsuccinimidyl-hexanote)-1'-methyl-3,3,3',3'-tetramethyl-indocarbcyanine-5,5'- disulfonate potassium with CE-LIF detection", Electrophoresis, 2007, vol. 28, pp. 822-829.
Gardner et al., "Total Synthesis of Petrobactin and its Homologues as Potential Growth Stimuli for Mannobacter hydrocarbonuclasticers. an Oil-Degrading Bacteria", J. Org. Chem., 2004, vol. 69, No. 10, pp. 3530-3537.
Greene, "Protection for the Amino Group", Protective Groups in Organic Synthesis, Chapter 7, John Wiley & Sons, New York, 1981, pp. 494-653.
Humora et al., "N2, N3-Di-tert-butoxycarbonlspermidine. A Synthesis of the Aglycone of the LL-BM123 Antibiotics", J. Org. Chem., 1979, vol. 44, No. 7, pp. 1100-1168.
Jung et al., "Practical synthesis of dyes for difference gel electrophoresis", Bioorganic & Medicinal Chemistry, 2006, vol. 14, pp. 92-97.
Kovar et al., "Characterization and performance of a near infrared 2-deoxyglucose optical imaging agent for mouse cancer models", Anal Biochem., Jan. 15, 2009, vol. 384, No. 2, pp. 254-262 (NIH Public Access Author Manuscript, 10 pages).
Lee et al., "Synthesis and Evaluation of Taxol-Folic Acid Conjugates as Targeted Antineoplastics", Bioorganic and Medicinal Chemistry, 2002, vol. 10, pp. 2397-2414.

(Continued)

*Primary Examiner* — Michael G Hartley
*Assistant Examiner* — Melissa Perreira
(74) *Attorney, Agent, or Firm* — Birch, Stewart, Kolasch & Birch, LLP

(57) ABSTRACT

The invention relates to fluorescent derivatives of cyanines conjugated with a polyamine group, having formula (I), or a pharmaceutically acceptable salt thereof. The invention also relates to the method for preparing said derivatives, diagnostic compositions containing same and the use thereof as a diagnostic probe for the detection of cancer tumors, in particular in vivo.

10 Claims, 1 Drawing Sheet
(1 of 1 Drawing Sheet(s) Filed in Color)

(56) References Cited

OTHER PUBLICATIONS

Levchine et al., "An Efficient Synthesis of Selectively Functionalized Spermidine", Synthesis, Jan. 1994, pp. 37-39.
Pittelkow et al., "Selective Synthesis of Carbarnate Protected Polyamines Using Alkyl Phenyl Carbonates", Synthesis, 2002, No. 15, pp. 2195-2202.
Sevick-Muraca et al., "Fluorescence-enhanced, near infrared diagnostic imaging with contrast agents", Current Opinion in Chemical Biology, 2002, vol. 6, pp. 642-650.
Weissieder, "A clearer vision for in vivo imaging: Process continues in the development of smaller, more penetrate probes for biological imaging", Nature Biotechnology, Apr. 2001, vol. 19, pp. 316-317.
International Search Report, mailed Jan. 30, 2012, issued in PCT/EP2011/070980.

* cited by examiner

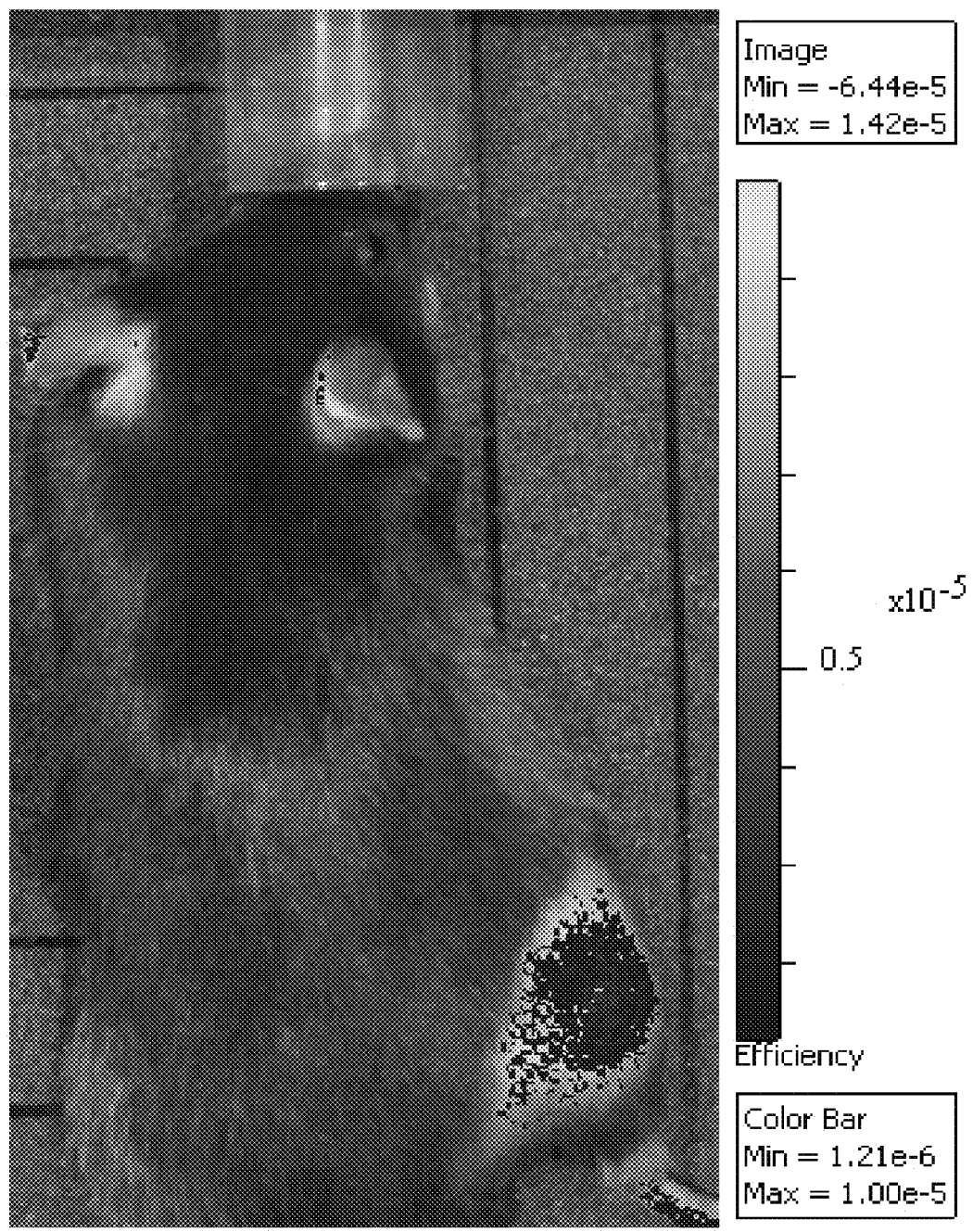

FLUORESCENT CYANINE-POLYAMINE DERIVATIVES AS A DIAGNOSTIC PROBE

The present invention relates to fluorescent cyanine-polyamine derivatives, the process for preparing same, diagnostic compositions containing same and the use thereof as a diagnostic probe for cancer.

Cancer continues to be one of the main causes of mortality in the Western world. In many cases, control means such as prevention, surgery, radiotherapy, immunotherapy and chemotherapy still do not eradicate the disease.

The reasons for this failure are partly due to the difficulty identifying and/or locating the tumour cell and treating the cell selectively without causing excessive damage to healthy tissue.

In vivo fluorescence imaging is a tool for identifying tumour tissue in relation to healthy tissue, using new optical imaging techniques. This technique advantageously used in preclinical surgery is in the process of being developed for the clinical stage. This fluorescent labelling approach is capable of detecting extremely small tumours. It is based on obtaining a tissue map in vivo using the fluorescence emission of a contrast medium, thus producing a three-dimensional image by reconstruction with an image analyser.

These exogenous contrast media, referred to as fluorophores, pass through the blood flow or lymph ducts and label target tissue such as cancer tumours for example.

Organic fluorophores are generally aromatic molecules having a significantly delocalised π electron system providing fluorescence properties in the visible range.

Cancer tumours are thus detected either merely by an accumulation of fluorophores due to an increase in vascularisation around the tumour, or by the expression of specific receptors or transporter to which the fluorophores binds.

Indeed, cancer cells require, for the proliferation thereof, a large number of essential biological elements including polyamines (spermine, spermidine, putrescine). Polyamines are essential for all dividing cells. The polyamines are produced from the amino acids contained in the cell. Arginine is converted to ornithine, ornithine undergoes decarboxylation to provide putrescine. This putrescine ($C_4$) may be extended with a $C_3$ chain by means of adenosine methionine, followed by decarboxylation providing spermidine, which may be further extended with a $C_3$ structural unit also by means of a further methionine residue providing spermine. These polyamines may also be broken down by oxidation with polyamine oxidases and thus convert into spermidine and putrescine. In normal situations, the endogenous polyamine synthesis is sufficient for the cell catabolism but in the case of cancer cells, the quantity of these polyamines available, essential for the development and growth of the cancer cell, is not sufficient and an exogenous intake of polyamines by means of a specific polyamine transporter is generally required. This transporter has a role in the intracellular importation of natural polyamines such as putrescine, spermidine and spermine. Since cancer cells need greater quantities of polyamines than healthy cells, they will thus be obtained from outside sources, involving polyamine transporter activity.

In this way, revealing this active transport makes it possible to detect cancer cells and monitor the progression thereof in terms of growth and dissemination. However, in human cells, the polyamine transporter has not been identified on a molecular level to date. The only method for demonstrating the presence thereof is thus that of using a probe recognised by the transporter which, by accumulating in the cell, will detect the activity thereof. Indeed, the transporter has a role in supply and regulation.

This specific polyamine transport phenomenon for tumour cells was described using an anticancer compound comprising an "epipodophyllotoxin" unit bound with spermine (*Cancer Res.* 2008, 68, 9845).

In the case, for example, of the compound in example 27 of the patent application WO 2005/100363, the "epipodophyllotoxin" structural unit grafted onto spermine does not appear to modify polyamine transporter recognition but makes it possible to internalise the compound in the tumour cell, so as to subsequently act as a cytotoxic agent. However, cancer tumours have extremely variable phenotypes and not all express the polyamine transporter to the same extent.

Using diagnostic probes, it is possible to identify in advance, i.e. prior to anti-tumour treatment, by means of fluorescence imaging, the tumour sites which would be susceptible to the treatment and those which would not.

The higher the fluorescence, the greater the susceptibility of the tumour in question to targeted anticancer treatment (for example, the compound in example 27 of the patent application WO 2005/100363).

Detecting this polyamine transport system thus makes it possible to select patients with tumours suitable for treatment with any anticancer compound vectorised by the polyamine transport system, regardless of the mode of action thereof.

Contrast media bearing a fluorescent unit conjugated with a deoxyglucose unit have previously been used in fluorescence imaging for selecting cancer cells expressing glucose transporter (GLUT) in vitro and in vivo (*Bioconjug. Chem.* 2006, 17, 662; *Bioconjug. Chem.* 2007, 18, 1303 and *Analytical Biochemistry* 2009, 384, 254-262).

Similarly, tumour cells have been detected in vitro using fluorescent probes such as those described in the patent application WO 2009/013360 having a fluorescent unit conjugated with a polyamine. These probes display fluorescence in the wavelength range λ~450-520 nm. While this spectral range is optimal for in vitro cellular studies, this part of the spectrum is not suitable for in vivo fluorescent imaging detection due to tissue and water absorption. The best operating range is situated in the red part of the visible spectrum. This window in the near infrared range (λ~650-900 nm) corresponds to low tissue absorption, prohibiting the use of probes displaying fluorescence in lower wavelengths, such as those described in WO 2009/013360. This window is also optimal for low water absorption, which becomes very high for wavelengths λ>1000 nm. Furthermore, accessibility to tissues situated in deep areas represents a challenge for selecting the suitable fluorophore (*Nature Biotech.* 2001, 19, 316; *Current Opin. in Chem. Biol.* 2002, 6, 642; *Cancer Res.* 2004, 64, 8009).

However, to the inventors' knowledge, there is no fluorescent probe available to date suitable for detecting in vivo, by fluorescence imaging, tumour cells expressing the polyamine transport system.

The problem addressed by the present invention is thus that of providing fluorescent compounds targeting the polyamine transport system and suitable for carrying out good-quality fluorescence medical imaging on humans in vivo.

After unsuccessful trials (see comparative example 13) demonstrating that not all fluorophores can be used, the inventors surprisingly discovered that conjugated hybrid cyanine-polyamine molecules specifically address this problem. Indeed, these molecules are internalised by the polyamine transport system and emit sufficient fluorescence in order to be readily detectable.

The present invention thus relates to compounds consisting of a polyamine unit bound to a substituted cyanine unit.

The substituted cyanine unit in these molecules bears the fluorescence suitable for in vivo imaging whereas the polyamine part of these molecules is recognised by the polyamine transport system, enabling the molecule to be internalised in the cancer cell. The tumour tissue labelled in this manner can be clearly differentiated from healthy tissue by means of fluorescence imaging and a tumour-to-muscle (healthy tissue) ratio can be determined.

Surprisingly, the compounds according to the present invention have a low level of involvement in chemical reactions in a physiological environment, for example in vivo, during measurement and do not give rise to a loss of fluorescence properties, i.e. a loss of signal, bleaching phenomenon.

Detecting the polyamine transport system thus makes it possible to select patients with tumours suitable for treatment with any anticancer compound vectorised by the polyamine transport system, regardless of the mode of action thereof.

Derivatives of cyanine 5-5 conjugated with polyamines were described in *Electrophoresis* 2007, 28, 822, without indicating any structure of these derivatives. Due to the nature of the substituents situated on the cyanine part, these derivatives are different to those according to the present invention. The non-conjugated cyanine 5-5 derivative is used for analysing and labelling the polyamine content of erythrocytes and for monitoring the carcinogenesis process in erythrocytes. Derivatives of cyanine 5.5 conjugated with polyamines are thus obtained during the analysis, conjugation being carried out directly in the sample to detect the presence of polyamine in erythrocytes. However, the use herein of derivatives of cyanine 5.5 conjugated with polyamines, which is one of the aims of the present invention, is different to that in this article and has never been previously mentioned.

The present invention thus relates to fluorescent derivatives consisting of a polyamine unit whereon a unit bearing fluorescence, a substituted cyanine, is bound, the process for preparing same, diagnostic compositions containing same and the use thereof for detecting tumours by fluorescence imaging, by targeting polyamine transporters. It also relates to means for selecting patients with such tumours, suitable for being treated with anticancer products vectorised by the polyamine system.

The present invention thus relates to fluorescent compounds having the following formula (I):

[chemical structure]

wherein:
R1 and R2, identical or different, represent a hydrogen atom, a halogen atom, a $C_{1-4}$alkyl, $C_{1-4}$alkoxy, aryl, nitro ($NO_2$), carboxyl (COOH) group; or represent an aromatic ring fused with the aromatic ring bearing them so as to form a naphthalene, R3 represents a $C_{1-6}$alkyl group optionally substituted with a —$SO_3H$ group, n equals 1 or 2, m equals 3, 4, 5 or 6, a, b, and c equal, independently of each other, 2, 3, 4, or 5, d and e equal, independently of one another, 0 or 1, on the condition that they are not both simultaneously equal to 0, and X represents a halogen atom, or a pharmaceutically acceptable salt thereof.

The term "halogen atom" refers, according to the present invention, to fluorine, chlorine, bromine and iodine atoms. It consists more particularly of a bromine, chlorine or iodine atom.

The term "$C_{1-6}$alkyl" group refers, according to the present invention, to a linear or branched saturated hydrocarbon chain, comprising 1 to 6 carbon atoms. Examples include the methyl, ethyl, propyl, isopropyl, butyl, isobutyl, sec-butyl, tert-butyl, pentyl or hexyl groups.

The term "$C_{1-4}$alkyle" groups refers, according to the present invention, to a linear or branched saturated hydrocarbon chain, comprising 1 to 4 carbon atoms. Examples include the methyl, ethyl, propyl, isopropyl, butyl, isobutyl, sec-butyl and tert-butyl groups.

The term "$C_{1-4}$alkoxy" group refers, according to the present invention, to a $C_{1-4}$alkyl group, as defined above, bound to the rest of the molecule by means of an oxygen atom. Examples include the methoxy, ethoxy, propoxy, isopropoxy, butoxy, isobutoxy, sec-butoxy and tert-butoxy groups.

The term "aryl" group refers, according to the present invention, to an aromatic group, preferably comprising 6 to 10 carbon atoms, and comprising one or a plurality of fused rings, such as a phenyl or naphthyl. Advantageously, it consists of phenyl.

In the present invention, "pharmaceutically acceptable" refers to that which is useful for preparing a composition intended to be administered to an animal, such as a mammal, including humans, which is generally safe, non-toxic and not biologically or otherwise undesirable and which is acceptable for veterinary use and for pharmaceutical or human diagnostic use.

The term "pharmaceutically acceptable salts" of a compound refers to salts which are pharmaceutically acceptable, as defined herein, and which have the sought pharmacological activity of the parent compound. Such salts comprise:

(1) hydrates and solvates, (2) acid addition salts formed with organic acids, such as formic acid, or inorganic acids such as hydrochloric acid or hydrobromic acid, or (3) salts formed when an acidic proton contained in the parent compound is either replaced by a metal ion, for example an alkaline metal ion, an alkaline-earth metal ion or an aluminium ion; or coordinated with an organic or inorganic base such as potassium hydroxide or sodium hydroxide.

In one particular embodiment of the invention, R1 and R2, identical or different, represent a hydrogen atom, a halogen atom, or a $C_{1-4}$alkyl, $C_{1-4}$alkoxy, aryl, nitro ($NO_2$), or carboxyl (COOH) group. Preferably, R1 and R2 are identical and each represent a hydrogen atom.

In a further particular embodiment of the invention, R3 represents a $C_{1-4}$alkyl group, for example methyl or butyl.

The compounds having formula (I) according to the invention may particularly be compounds for which m equals 5.

In particular, a, b and c may, independently of each other, take the values 3 or 4.

In one particular embodiment of the invention, when d equals 0 and e equals 1, a and b equal, independently of one another, 3 or 4.

In a further particular embodiment of the invention, when d equals 1 and e equals 0, a equals 3 or 4.

In a further particular embodiment of the invention, when d equals 1 and e equals 1 and a equals 3, b equals 4 and c equals 3.

X represents more particularly a bromine or iodine atom.

The pharmaceutically acceptable salt of a compound having formula (I) may be a hydrochloric acid addition salt, a plurality of HCl molecules may be incorporated in the compound having formula (I) according to the number of amine functions (NH or $NH_2$) comprised therein. The pharmaceutically acceptable salt may thus be a mono-, di-, tri- or tetra-hydrochloride.

The present invention particularly relates to the following compounds having the formula (I):
1) 1-(6-(3-(4-(3-aminopropylamino)butylamino)propylamino)-6-oxohexyl) 2-((1E,3E,5E)-5-(1-methyl-3,3-dimethylindolin-2-ylidene)penta-1,3-dienyl)-3,3-dimethyl-3H-indolium iodide,
2) 1-{5-[4-(3-aminopropylamino)-butylcarbamoyl]-pentyl}-3,3-dimethyl-2-{(1E,3E)-5-[1,3,3-trimethyl-1,3-dihydroindol-(2E)-ylidene]-penta-1,3-dienyl}-3H-indolium iodide,
3) 1-{5-[3-(4-aminobutylamino)-propylcarbamoyl]-pentyl}-3,3-dimethyl-2-{(1E,3E)-5-[1,3,3-trimethyl-1,3-dihydroindol-(2E)-ylidene]-penta-1,3-dienyl}-3H-indolium iodide,
4) 1-{5-[4-amino-butylcarbamoyl]-pentyl}-3,3-dimethyl-2-{(1E,3E)-5-[1,3,3-trimethyl-1,3-dihydroindol-(2E)-ylidene]-penta-1,3-dienyl}-3H-indolium iodide,
5) 1-(6-(3-(4-(3-aminopropylamino)butylamino)propylamino)-6-oxohexyl)2-((1E,3E,5E)-5-(1-butyl-3,3-dimethylindolin-2-ylidene)penta-1,3-dienyl)-3,3-dimethyl-3H-indolium bromide,
6) 1-{5-[4-(3-aminopropylamino)-butylcarbamoyl]-pentyl}-3,3-dimethyl-2-{(1E,3E)-5-[1-butyl-3,3-dimethyl-1,3-dihydroindol-(2E)-ylidene]-penta-1,3-dienyl}-3H-indolium bromide,
7) 1-{5-[4-amino-butylcarbamoyl]-pentyl}-3,3-dimethyl-2-{(1E,3E)-5-[1-butyl-3,3-dimethyl-1,3-dihydroindol-(2E)-ylidene]-penta-1,3-dienyl}-3H-indolium bromide,
8) 1-(5-{3-[4-(3-aminopropylamino)butylamino]-propylcarbamoyl}-pentyl)-2-{(1E,3E,5E)-7-[1,3,3-trimethyl-1,3-dihydroindol-(2E)-ylidene]-hepta-1,3,5-trienyl}-3,3-dimethyl-3H-indolium iodide,
9) 1-{5-[4-(3-aminopropylamino)-butylcarbamoyl]-pentyl}-3,3-dimethyl-2-{(1E,3E,5E)-7-[1,3,3-trimethyl-1,3-dihydroindol-(2E)-ylidene]-hepta-1,3,5-trienyl}-3H-indolium iodide,
10) 1-{5-[3-(4-aminobutylamino)-propylcarbamoyl]-pentyl}-3,3-dimethyl-2-{(1E,3E,5E)-7-[1,3,3-trimethyl-1,3-dihydroindol-(2E)-ylidene]-hepta-1,3,5-trienyl}-3H-indolium iodide,
11) 1-[5-(4-aminobutylcarbamoyl)-pentyl]-3,3-dimethyl-2-{(1E,3E,5E)-7-[1,3,3-trimethyl-1,3-dihydroindol-(2E)-ylidene]-hepta-1,3,5-trienyl}-3H-indolium iodide,
12) 1-(5-{3-[4-(3-aminopropylamino)butylamino]-propylcarbamoyl}-pentyl)-2-{(1E,3E,5E)-7-[1-butyl-3,3-dimethyl-1,3-dihydroindol-(2E)-ylidene]-hepta-1,3,5-trienyl}-3,3-dimethyl-3H-indolium bromide,
13) 1-{5-[4-(3-aminopropylamino)-butylcarbamoyl]-pentyl}-3,3-dimethyl-2-{(1E,3E,5E)-7-[1-butyl-3,3-dimethyl-1,3-dihydroindol-(2E)-ylidene]-hepta-1,3,5-trienyl}-3H-indolium bromide,
14) 1-{5-[3-(4-aminobutylamino)-propylcarbamoyl]-pentyl}-3,3-dimethyl-2-{(1E,3E,5E)-7-[1-butyl-3,3-dimethyl-1,3-dihydroindol-(2E)-ylidene]-hepta-1,3,5-trienyl}-3H-indolium bromide, and
15) 1-[5-(4-aminobutylcarbamoyl)-pentyl]-2-{(1E,3E,5E)-7-[1-butyl-3,3-dimethyl-1,3-dihydroindol-(2E)-ylidene]-hepta-1,3,5-trienyl}-3,3-dimethyl-3H-indolium bromide, or a pharmaceutically acceptable salt thereof, such as a hydrochloric acid addition salt.

The invention also relates to a diagnostic composition comprising at least one compound having formula (I) according to the invention or a pharmaceutically acceptable salt thereof and at least one pharmaceutically acceptable excipient.

The term "diagnostic composition" refers, according to the present invention, to a composition intended to be administered to a patient, particularly a human, with a view to enabling diagnostics, more particularly in vivo diagnostics. Within the scope of the present invention, it would consist particularly of enabling the detection of cancer tumours.

The diagnostic compositions according to the invention may preferentially be formulated for parenteral administration, preferentially intravenous, intended for mammals, including humans.

The active ingredient may be administered in unitary administration forms, mixed with conventional pharmaceutical carriers, to animals or humans.

For intravenous administration, aqueous suspensions, isotonic saline solutions or sterile solutions suitable for injection containing pharmacologically compatible dispersion agents and/or wetting agents will particularly be used.

The compounds according to the invention used as diagnostic agents may be used at doses between 0.01 mg and 1000 mg. The dose administered may be advantageously between 5 mg and 500 mg, and particularly between 10 mg and 200 mg. It may be necessary to use doses outside these ranges, which would be obvious for those skilled in the art.

The present invention also relates to the use of a compound having formula (I) according to the invention or a pharmaceutically acceptable salt thereof as a diagnostic probe for medical imaging, particularly fluorescence imaging, more particularly for detecting cancer tumours expressing the polyamine transport system in vivo or in vitro, particularly in vivo.

The present invention also relates to compounds having formula (I) according to the invention or a pharmaceutically acceptable salt thereof for use in diagnosing, particularly in vivo, a tumour expressing the polyamine transport system, particularly by medical imaging, such as fluorescence imaging.

The present invention also relates to the use of a compound having formula (I) according to the invention for preparing a diagnostic composition for detecting a cancer tumour expressing the polyamine transport system, more particularly in vivo, particularly by medical imaging, such as by fluorescence.

The present invention also relates to a method for detecting (diagnostic method) in vivo a cancer tumour expressing the polyamine transport system by administering a sufficient quantity of a compound having formula (I) according to the invention or a pharmaceutically acceptable salt thereof to a person in need thereof.

This administration is followed by a step for detecting the fluorescence emitted by the compound having formula (I) by fluorescence medical imaging so as to view the tumour.

Finally, the present invention relates to a process for synthesising compounds having formula (I) according to the invention comprising the following successive steps:

(i) coupling between a compound having the following formula (VII):

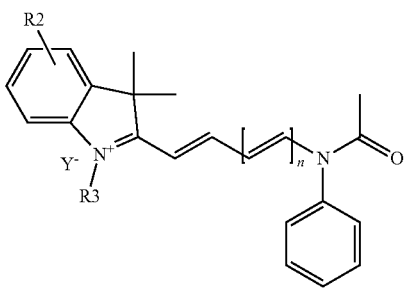

(VII)

wherein R2, R3 and n are as described above, and Y represents a halogen atom, and in particular a bromine or iodine atom, where Y is advantageously identical to X, with a compound having the following formula (V):

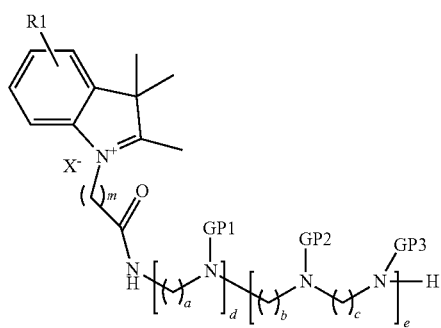

(V)

wherein R1, X, m, a, b, c, d and e are as defined above and GP1, GP2 and GP3, identical or different, represent an N-protecting group, to obtain a compound having the following formula (VIII):

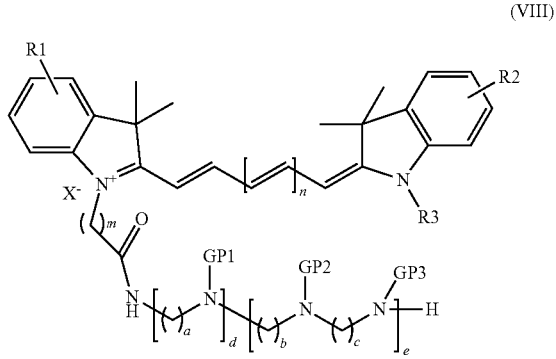

(VIII)

wherein, R1, R2, R3, X, m, n, a, b, c, d, e, GP1, GP2 and GP3 are as defined above, (ii) deprotecting the amine functions protected by the groups GP1, GP2 and GP3 in the compound having formula (VIII) obtained in step (i) above to obtain a compound having formula (I) according to the invention, (iii) optionally salifying the compound having formula (I) obtained in step (ii) above to obtain a pharmaceutically acceptable salt thereof, and (iv) separating the compound having formula (I) or a pharmaceutically acceptable salt thereof obtained in the previous step from the reaction medium.

The term "N-protecting group" refers, according to the present invention, to any substituent protecting the NH or $NH_2$ group against undesirable reactions such as the N-protecting groups described in Greene, "Protective Groups In Organic synthesis", (John Wiley & Sons, New York (1981)) and Harrison et al. "Compendium of Synthetic Organic Methods", Vols. 1 to 8 (J. Wiley & sons, 1971 to 1996), this publication also describing the methods for deprotecting these protecting groups. N-protecting groups comprise carbamates, amides, N-alkylated derivatives, aminoacetal derivatives, N-benzylated derivatives, imine derivatives, enamine derivatives and N-heteroatom derivatives. In particular, the N-protecting group comprises formyl, acetyl, benzoyl, pivaloyl, phenylsulfonyl, benzyl (Bn), t-butyloxycarbonyl (BOC), benzyloxycarbonyl (Cbz), p-methoxybenzyloxycarbonyl, p-nitrobenzyl-oxycarbonyl, trichloroethoxy carbonyl (TROC), allyloxycarbonyl (Alloc), 9-fluorenylmethyloxycarbonyl (Fmoc), trifluoro acetyl, benzyl carbamates (optionally substituted) and similar. It may particularly consist of a Boc or Alloc group.

Step (i):
The coupling may be carried out in a solvent such as ethanol, in the presence of sodium acetate.

Step (ii):
Preferably, the GP1, GP2 and GP3 groups are identical and may represent a BOC or Alloc group which may be deprotected in an acidic medium, particularly in the presence of hydrochloric acid or trichloroacetic acid.

Step (iii):
This step may be carried out by reacting the compound having formula (I) obtained in step (ii) with a pharmaceutically acceptable acid or base. It will preferably consist of a pharmaceutically acceptable acid such as hydrochloric acid.

According to the nature of the protecting groups GP1, GP2 and GP3 and the pharmaceutically acceptable salt sought, it may be envisaged to perform steps (ii) and (iii) in a "one-pot" manner, i.e. in the same reactor, without isolating the synthesis intermediate between the two steps, and particularly using the same reagents (namely the same acid for deprotecting the groups GP1, GP2 and GP3 and for forming the pharmaceutically acceptable salt).

Step (iv):
The compound obtained may be separated from the reaction medium by means of methods well-known to those skilled in the art, such as for example by extraction, solvent evaporation or by precipitation and filtration.

Moreover, the compound may be purified if required using techniques well-known to those skilled in the art, such as by recrystallisation if the compound is crystalline, by distillation, by silica gel column chromatography or by high-performance liquid chromatography (HPLC).

The compound having formula (V) may be prepared by means of peptide coupling between a compound having the following formula (III):

(III)

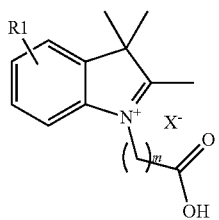

wherein R1, m and X are as defined above, with a protected polyamine having the following formula (IX):

(IX)

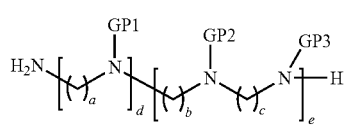

wherein GP1, GP2, GP3, a, b, c, d and e are as defined above, or a (organic or inorganic as described above) acid addition salt thereof such as a hydrochloride.

The peptide coupling may be carried out in the presence of a coupling agent, such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), 2-(1H-benzotriazole-1-yl)-1,1,3,3-tetramethyluronium hexafluorophosphate (HBTU), 2-(1H-benzotriazole-1-yl)-1,1,3,3-tetramethyluronium tetrafluoroborate (TBTU) or O-(7-azobenzotriazol-1-yl)-1,1,3,3-tetramethyluronium hexafluorophosphate (HATU), optionally associated with a coupling auxiliary such as N-hydroxy succinimide (NHS), N-hydroxy benzotriazole (HOBt), 3,4-dihydro-3-hydroxy-4-oxo-1,2,3-benzotriazole (HOOBt), 1-hydroxy-7-azabenzotriazole (HAt) or N-hydroxysulfosuccinimide (sulfo NHS). In particular, the coupling may be carried out in the presence of TBTU.

Moreover, the coupling may be carried out in the presence of a base such as triethylamine. An inert solvent such as acetonitrile may be used.

Polyamines are commercially available and may be protected by means of techniques well-known to those skilled in the art enabling ready access to the compounds having formula (IX). An example of a polyamine derivative, spermine protected with three BOC groups, is described in *Tetrahedron Lett.* 1998, 39, 439.

The compounds having formula (III) may be prepared from an indoline having the following formula (IIa):

(IIa)

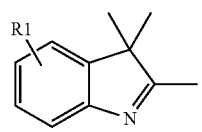

wherein R1 is as defined above, by reacting with an acid having the following formula (X):

(X)

wherein m and X are as defined above.

This coupling is notably carried out without a solvent, merely by mixing the two reagents having formulas (IIa) and (X), more particularly at a high temperature, namely between 80 and 150° C.

The indolines having formula (IIa) and the acids having formula (X) are either commercially available, or readily accessible using techniques well-known to those skilled in the art.

The compound having formula (VII) may be obtained by coupling between a compound having the following formula (IV):

(IV)

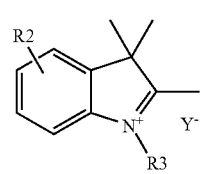

wherein R2, R3 and Y are as defined above,
and a compound having the following formula (VI):

(VI)

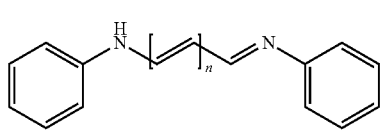

wherein n is as defined above, or a (organic or inorganic as described above) acid addition salt thereof such as a hydrochloride.

This coupling may be carried out in the presence of acetic anhydride and acetic acid, particularly under reflux.

The compounds having formula (IV) may be prepared from an indoline having the following formula (IIb):

(IIb)

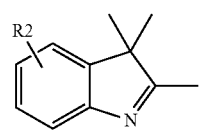

wherein R2 is as defined above,
by reacting with a reagent having the formula R3-Y wherein R3 and Y are as defined above.

This coupling is notably carried out without a solvent, merely by mixing the two reagents, more particularly at a high temperature, namely between 80 and 150° C.

The indolines having formula (IIa) and the reagents having the formula R3-Y are either commercially available, or readily accessible using techniques well-known to those skilled in the art.

The compounds having formula (VI) may be prepared by reacting aniline, a commercially available product, with a diacetal having the following formula (XI):

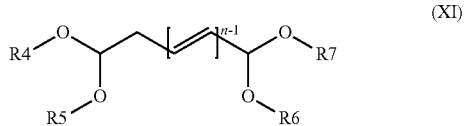

(XI)

wherein n is as defined above and R4, R5, R6 and R7, identical or different, represent a $C_{1-6}$alkyl group, preferably $C_{1-4}$alkyl such as methyl, or (R4 and R5) and/or (R6 and R7) form a $—(CH_2)_p—$ chain together, where p represents 2 or 3.

In particular, R4, R5, R6 and R7 are all identical and particularly represent a $C_{1-4}$alkyl group such as methyl.

Aniline should be used at a rate of at least two molar equivalents with respect to diacetal, i.e. at least two moles of aniline are used for each mole of diacetal used.

The diacetal having formula (XI) is either commercially available, or accessible using techniques well-known to those skilled in the art, particularly from the corresponding dialdehyde.

The synthesis of compounds having formula (I) is notably presented in the following general diagram:

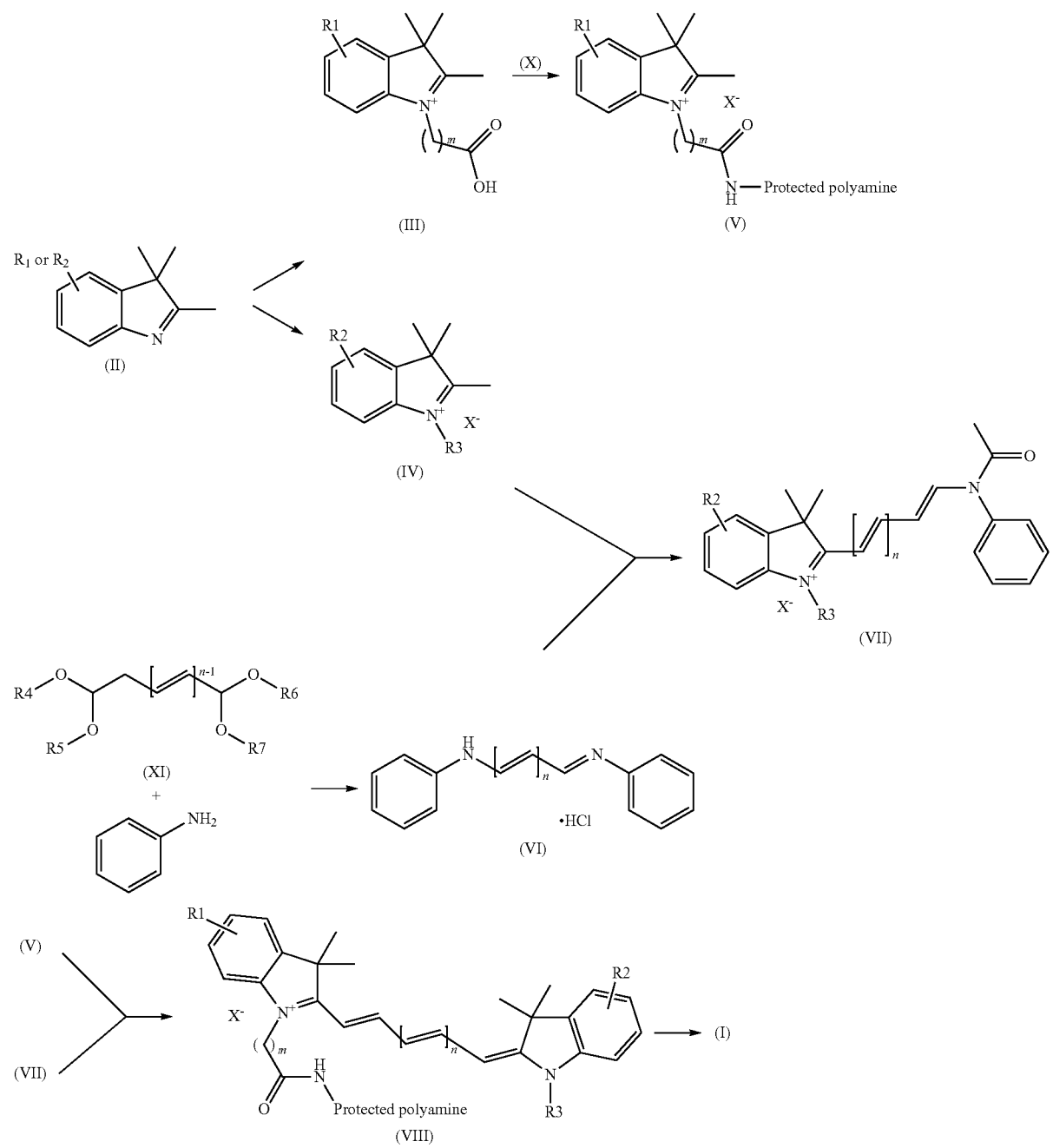

The examples hereinafter describe the various stages for the preparation of compounds according to the invention and merely serve to illustrate the invention and are in no way limiting.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 1 represents the fluorescence image of a mouse with a tumour, 24 hours after injection of the probe F98942 (example 7) (50 μg) intravenously. The arrow indicates the tumour.

EXAMPLES

The following abbreviations have been used in the experimental part hereinafter:
APCI Atmospheric pressure chemical ionisation
BOC tert-Butyloxycarbonyl
TLC Thin Layer Chromatography
DMSO Dimethyl sulfoxide
ESI Electrospray ionisation
HPLC High-Performance Liquid Chromatography
Yd Yield
Rf Ratio-to-front
NMR Nuclear Magnetic Resonance
TBTU 2-(1H-Benzotriazole-1-yl)-1,1,3,3-tetramethyluronium tetrafluoroborate
THF Tetrahydrofuran I-Summary of Compounds According to the Invention Example 1

1-(6-(3-(4-(3-aminopropylamino)butylamino)propylamino)-6-oxohexyl)-2-((1E,3E,5E)-5-(1-butyl-3,3-dimethylindolin-2-ylidene)penta-1,3-dienyl)-3,3-dimethyl-3H-indolium bromide Compound having formula (I) where R1=R2=H, R3=nBu, n=1, m=5, X=Br, d=e=1, a=3, b=4, and c=3.

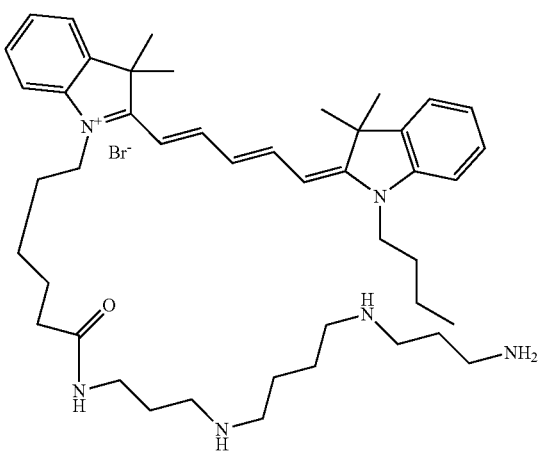 [SMILES: CCCCN1/C(=C/C=C/C=C/C2=[N+](CCCCCC(=O)NCCCNCCCCNCCCN)c3ccccc3C2(C)C)C(C)(C)c2ccccc21 ; [Br-]]

Stage 1—
Preparation of triBOC-spermine hydrochloride (*Bioorg. Med. Chem.* 2002, 10, 2397). Compound having formula (IX) where P=COOtBu, a=3, b=4, c=3, and d=e=1.

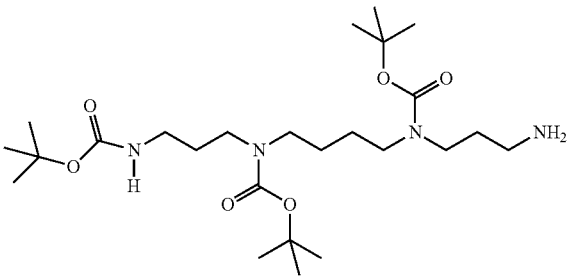 [SMILES: CC(C)(C)OC(=O)NCCCN(CCCCN(CCCN)C(=O)OC(C)(C)C)C(=O)OC(C)(C)C]

40 g of spermine is placed in solution in 300 mL of $CH_2Cl_2$ and cooled to 0° C. 23.8 mL of ethyl trifluoroacetate in solution in 50 mL of $CH_2Cl_2$ is added, drop by drop. The solution is then left under stirring for 1 hour at ambient temperature. The residue obtained is taken up with 600 mL of THF, and 140.28 mL of triethylamine is introduced. A solution of 174.48 g of $BOC_2O$ in 200 mL of THF is then introduced while maintaining the temperature at 20° C. Stirring at ambient temperature is maintained for a further three hours, and the reaction medium is poured onto water and extracted with isopropyl ether. After settling, drying on sodium sulphate, filtration and evaporation, the organic solution is evaporated. The residue obtained is then taken up with 900 mL of an 8:2 $MeOH/H_2O$ mixture. 192.6 g of caesium carbonate is added and the whole is heated to reflux for three hours. After evaporating the methanol at reduced pressure, water is added and extraction with isopropyl ether is performed. The organic phase is settled, and 0.5 N hydrochloric acid is introduced into this organic phase. The whole is allowed to settle. Three phases appear. The middle phase in oily form contains the product sought in hydrochloride form. This phase is settled, and then taken up with $CH_2Cl_2$, and dried on sodium sulphate. After filtration and evaporation, 54 g of triBOC spermine hydrochloride in the form of a colourless oil is obtained and is used directly in the following step (Yd=50%).

$SiO_2$ TLC: $CH_2Cl_2$—MeOH—$NH_4OH$ (90-10-10)—Rf=0.5.

$C_{25}H_{50}N_4O_6$, HCl: 539.17—(Mass APCI+500° C. $MH^+$=503.4).

Stage 2—
Preparation of 1-(5-carboxypentyl)-2,3,3-trimethyl-3H-indolium bromide (*Bioorg. Med. Chem.* 2006, 4, 92-97). Compound having formula (III) where R1=H, m=5, and X=Br.

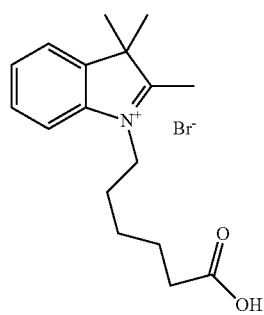 [SMILES: CC1=[N+](CCCCCC(=O)O)c2ccccc2C1(C)C ; [Br-]]

1.6 g of 2,3,3-trimethylindolenine and 2 g of bromohexanoic acid are heated to boiling point for 3 hours at 120° C. Bulking of the medium is observed. The reaction medium is crystallised in ethyl acetate, filtered, washed with acetone and then with isopropyl ether. After vacuum-drying, 2.3 g of pinkish solid is obtained (Yd=64.6%).

$C_{17}H_{24}NO_2$ 274.32—(Mass ESI+400° C. M=274.1).

Stage 3—

Preparation of 1-(9,14-bis(tert-butoxycarbonyl)-2,2-dimethyl-4,19-dioxo-3-oxa-5,9,14,18-tetraazatetracosan-24-yl)-2,3,3-trimethyl-3H-indolium bromide. Compound having formula (V) where R1=H, m=5, and X=Br, the protected polyamine consists of the compound having formula (IX) where P=COOtBu, d=e=1, a=3, b=4, and c=3.

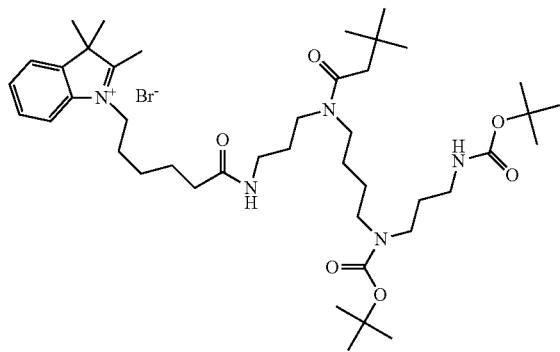 [SMILES: CC1=[N+](CCCCCC(=O)NCCCN(CCCCN(CCCNC(=O)OC(C)(C)C)C(=O)OC(C)(C)C)C(=O)CC(C)(C)C)c2ccccc2C1(C)C ; [Br-]]

To the mixture of 1 g of tri-BOC-spermine hydrochloride obtained previously in stage 1, 0.5 g of the compound from the preparation of stage 2 above and 0.6 mL of triethylamine in solution in 30 mL of acetonitrile, 0.6 g of TBTU is added in one go at ambient temperature. The whole is left in contact at ambient temperature for 3 hours. The reaction medium is hydrolysed with a saturated $NaHCO_3$ solution and then extracted with ethyl acetate. The organic phase after settling is washed with a 1N HCl solution, settled and dried on anhydrous sodium sulphate. After filtration and evaporation at reduced pressure, the residue obtained is fixed on silica for purification by flash chromatography (gradient 100% heptane to 100% ethyl acetate). The fractions concerned by the product are evaporated at reduced pressure to produce 1.2 g of brown oil (Quantitative Yd).

$C_{42}H_{72}BrN_5O_7$: 838.98—(Mass ESI+400° C. M=758.6).

Stage 4—

Preparation of 1-butyl-2,3,3-trimethyl-3H-indolium bromide. Compound having formula (IV) where R2=H, R3=nBu, and X=Br.

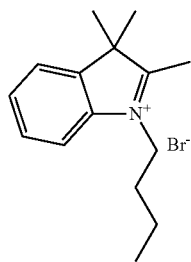 [SMILES: CCCC[N+]1=C(C)C(C)(C)c2ccccc21 ; [Br-]]

8 g of 2,3,3-trimethylindolenine and 6.9 g of bromobutane are heated to boiling point for 8 hours at 110° C. The gummy reaction medium obtained is crystallised in ethyl acetate under stirring for 1 hour, filtered, and washed with isopropyl ether. After vacuum-drying, 7 g of purplish-blue red solid is obtained (Yd=47%).

$C_{15}H_{22}BrN$: 296.26 (Mass detected: APCI+500° C. M=216.2).

$^1$H NMR (400 MHz, DMSO d6) δ=8.01 (1H, dd, H-7), 7.85 (1H, dd, H-4), 7.63 (4H, H-5, H-6), 4.47 (2H, t, H-1'), 2.86 (3H, s, CH3), 1.82 (2H, m, H-2'), 1.55 (6H, s, 2×CH3) 1.44 (2H, m, H-3'), 0.94 (3H, t, H-4').

Stage 5—

Preparation of 3-(phenylamino)allylidene)aniline hydrochloride (*Bioorg. Med. Chem.* 2006, 4, 92-97). Compound having formula (VI) where n=1.

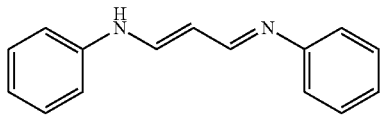 [SMILES: C(=C\Nc1ccccc1)/C=N/c1ccccc1]

24.7 g of aniline in solution in 300 mL of 0.75 N HCl is added drop by drop to 21.8 g of 1,1,3,3-tetramethoxypropane in solution in 300 mL of 0.75 N HCl. The appearance of an intense orange colour and the precipitation of an orange crystalline solid are observed. The medium is then left under stirring for 3 hours at 50° C. The cooled medium is filtered, vacuum-dried to obtain 15.2 g of orange solid (Yd=44.2%).

$C_{15}H_{14}N_2$, HCl—(Mass ESI+400° C. MH$^+$=223.1).

Stage 6—

Preparation of 1-butyl-3,3-dimethyl-2-((1E,3E)-4-(N-phenylacetamido)buta-1,3-dienyl)-3H-indolium bromide. Compound having formula (VII) where R2=H, R3=nBu, X=Br, and n=1.

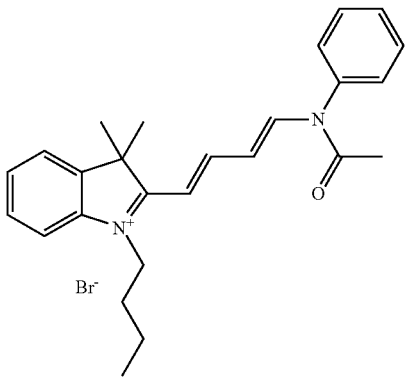 [SMILES: CCCC[N+]1=C(/C=C/C=C/N(C(C)=O)c2ccccc2)C(C)(C)c2ccccc21 ; [Br-]]

A mixture of 3 g of the preparation from stage 4 above with 5.2 g of the preparation from stage 5 above in solution in 45 mL of 2:1 acetic anhydride and acetic acid mixture is heated to reflux for 2 hours. The solvent is evaporated at reduced pressure and the residue obtained is fixed on silica for purification by means of flash chromatography (gradient on silica: 100% ethyl acetate to 90:10 ethyl acetate/methanol). The fractions in question are evaporated to obtain 3.6 g of crystallising scarab red oil (Yd=77.7%). $C_{26}H_{31}BrN_2O$: 467.454.

Stage 7—

Preparation of 1-(9,14-bis(tert-butoxycarbonyl)-2,2-dimethyl-4,19-dioxo-3-oxa-5,9,14,18-tetraazatetracosan-24-yl)-2-((1E,3E,5E)-5-(1-butyl-3,3-dimethylindolin-2-ylidene) penta-1,3-dienyl)-3,3-dimethyl-3H-indolium bromide. Compound having formula (VIII) where R1=R2=H, R3=nBu, X=Br, n=1, and m=5, the protected polyamine consists of the compound having formula (IX) where P=COOtBu, d=e=1, a=3, b=4, and c=3.

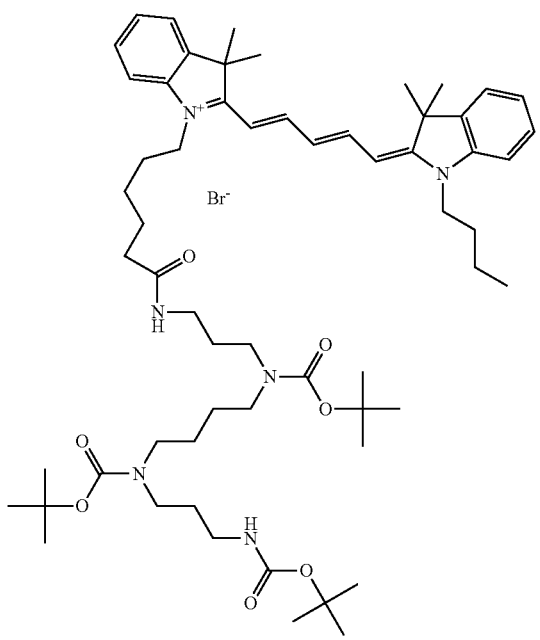 [SMILES: CCCCN1/C(=C/C=C/C=C/C2=[N+](CCCCCC(=O)NCCCN(CCCCN(CCCNC(=O)OC(C)(C)C)C(=O)OC(C)(C)C)C(=O)OC(C)(C)C)c3ccccc3C2(C)C)C(C)(C)c2ccccc21 ; [Br-]]

A mixture of 2.4 g of the preparation from stage 3 above and 1.5 g of the preparation from stage 6 above in solution in 40 mL of ethanol in the presence of 1.4 g of sodium acetate is left under stirring at ambient temperature for approximately 1 hour. After adding silica, the product is fixed thereon by evaporating ethanol at reduced pressure. The product is purified by means of SiO$_2$ flash chromatography (gradient: 100% ethyl acetate to 75% ethyl acetate—25% methanol). The fractions in question are evaporated at reduced pressure to obtain 1.5 g of scarab blue solid (Yd=48%).

$C_{60}H_{93}BrN_6O_7$: 1090.35—(Mass APCI+500° C. M=1009.9).

Stage 8—

Preparation of 1-(6-(3-(4-(3-aminopropylamino)butylamino)propylamino)-6-oxohexyl)2-((1E,3E,5E)-5-(1-butyl-3,3-dimethylindolin-2-ylidene)penta-1,3-dienyl)-3,3-dimethyl-3H-indolium bromide trihydrochloride. Compound having formula (I) where R1=R2=H, R3=nBu, n=1, m=5, d=e=1, a=3, b=4, c=3, and X=Br.

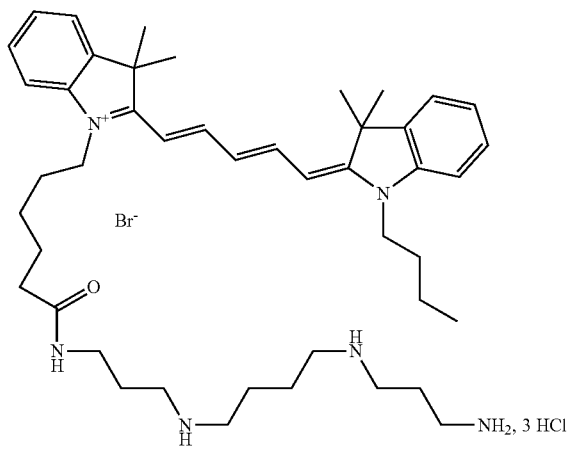 [SMILES: CCCCN1/C(=C/C=C/C=C/C2=[N+](CCCCCC(=O)NCCCNCCCCNCCCN)c3ccccc3C2(C)C)C(C)(C)c2ccccc21 ; [Br-]]

1.5 g of preparation 7 above in solution in 100 mL of dichloromethane is left in contact for 2 hours under stirring at ambient temperature in the presence of 10 mL of a 4M HCl/dioxane solution. The solvent is evaporated at reduced pressure to obtain a residue which is crystallised in ethyl acetate. After filtration and vacuum-drying, 1 g of deep blue solid in trihydrochloride form is obtained.

Purification is performed by means of preparative HPLC on an X-bridge C-18 10μ, 30×250 mm column, λ: 220 nm, flow rate: 40 mL/min. Mobile phase gradient: 100% 5 mM HCl to 80% 5 mM HCl-20% acetonitrile. The fractions in question are freeze-dried after removing the acetonitrile at reduced pressure. The freeze-dried product is taken up with ethyl acetate, filtered and vacuum-dried to obtain 440 mg of deep purple solid (Yd=35.6%).

Analytical HPLC purity: 98.5% C8-X-bridge 5 micron 4.6×250 mm column. λ: 220 nm—mobile phase 60% 6.8 g/L pH 4 KH$_2$PO$_4$ buffer—40% CH$_3$CN. Retention time: 7.56 min.

$^1$H NMR (400 MHz, D$_2$O) δ=8.015 (2H, t, J=12.8 Hz, H-14, H-14'), 7.53 (2H, m, J=7.2 Hz, H-6, H-6'), 7.42 (H-5, 5'), 7.26-7.33 (4H, m, H-3, H-3', H-4, H-4'), 6.51 (1H, t, J=12.4 Hz, H-15'), 6.26 (1H, d, J=13.6 Hz, H-13), 6.23 (1H, d, J=13.6 Hz, H-13'), 4.08 (4H, m, H-10, H-10'), 2.85-3.18 (12H, m, H-7", H-9", H-11", H-14", H-16", H-18"), 2.25 (2H, t, J=7.2 Hz, H-4"), 2.10 (2H, quin, J=7.4 Hz, H-17"), 1.78-1.85 (8H, m, H-1", H-8", H-11, H-13"), 1.64 (12H, s, CH3×4), 1.37-1.48 (4H, m, H-3"), 1.15 (2H, d, H-12), 0.97 (3H, t, H-13)

$C_{45}H_{69}BrN_6O$, 3HCl: 899.39 (Mass APCI+500° C.: M=709.5).

Example 2

1-(6-(3-(4-(3-aminopropylamino)butylamino)propylamino)-6-oxohexyl) 2-((1E,3E,5E)-5-(1-methyl-3,3-dimethylindolin-2-ylidene)penta-1,3-dienyl)-3,3-dimethyl-3H-indolium iodide Compound having formula (I) where R1=R2=H, R3=Me, X=I, n=1, m=5, d=e=1, a=3, b=4, and c=3.

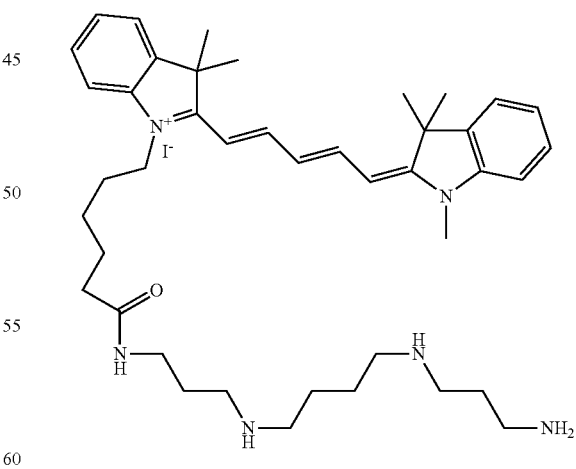

Stage 1:

Preparation of 1-methyl-3,3-dimethyl-2-((1E,3E)-4-(N-phenylacetamido)buta-1,3-dienyl)-3H-indolium iodide (*Bioorg. Med. Chem.* 2006, 4, 92-97).

Compound having formula (VII) where R2=H, R3=Me, X=I, and n=1.

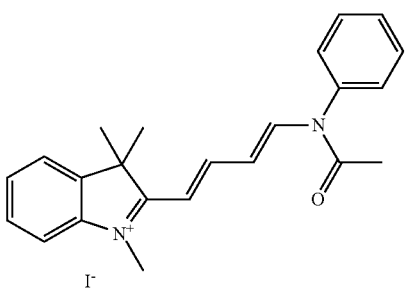 [SMILES: CC(=O)N(/C=C/C=C/C1=[N+](C)c2ccccc2C1(C)C)c1ccccc1 ; [I-]]

A mixture of 2 g of tetramethyl indolenium iodide with 3.4 g of the preparation from stage 5 of example 1, in solution in 30 mL of 2:1 acetic anhydride and acetic acid mixture is heated to reflux for 2 hours. The solvent is evaporated at reduced pressure and the residue obtained is fixed on silica for purification by flash chromatography (gradient on silica: 100% ethyl acetate to 90:10 ethyl acetate/methanol). The fractions in question are evaporated to obtain 2 g of black solid (Yd=64%).

$C_{23}H_{25}N_2O$: 472.361—(Mass ESI+400° C.: M=345.2).

Stage 2:

Preparation of 1-(9,14-bis(tert-butoxycarbonyl)-2,2-dimethyl-4,19-dioxo-3-oxa-5,9,14,18-tetraazatetracosan-24-yl)-2-(1E,3E,5E)-5-(1-butyl-3,3-dimethylindolin-2-ylidene)penta-1,3-dienyl)-3,3-dimethyl-3H-indolium iodide. Compound having formula (VIII) where R1=R2=H, R3=Me, X=I, n=1, and m=5, the protected polyamine consists of the compound having formula (IX) where P=COOtBu, d=e=1, a=3, b=4, and c=3.

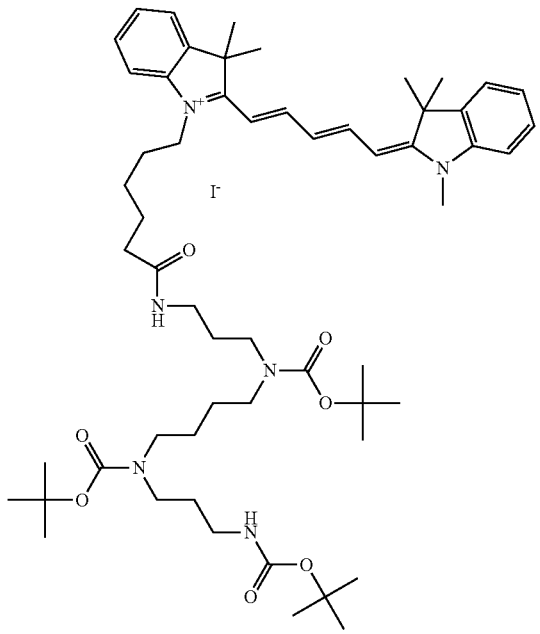 [SMILES: CN1/C(=C/C=C/C=C/C2=[N+](CCCCCC(=O)NCCCN(CCCCN(CCCNC(=O)OC(C)(C)C)C(=O)OC(C)(C)C)C(=O)OC(C)(C)C)c3ccccc3C2(C)C)C(C)(C)c2ccccc21 ; [I-]]

A mixture of 0.17 g of the preparation from stage 3 of example 1 and 0.1 g of the preparation from stage 1 of this example, in solution in 15 mL of ethanol in the presence of 0.2 g of sodium acetate is left under stirring at ambient temperature for approximately 4 hours. After adding silica, the product is fixed thereon by evaporating ethanol at reduced pressure. The product is purified by means of $SiO_2$ flash chromatography (gradient: 100% ethyl acetate to 75% ethyl acetate—25% methanol). The fractions in question are evaporated at reduced pressure to obtain 0.1 g of scarab blue solid (Yd=45%).

$C_{57}H_{87}IN_6O_7$: 1095.24—(Mass ESI+400° C. M=967.6).

$SiO_2$ TLC: 5/1/1 $CH_2Cl_2/CH_3OH$/Heptane—Rf: 0.65.

Stage 3:

Preparation of 1-(6-(3-(4-(3-aminopropylamino)butylamino)propylamino)-6-oxohexyl)2-((1E,3E,5E)-5-(1-methyl-3,3-dimethylindolin-2-ylidene)penta-1,3-dienyl)-3,3-dimethyl-3H-indolium iodide trihydrochloride. Compound having formula (I) where R1=R2=H, R3=Me, X=I, n=1, m=5, d=e=1, a=3, b=4, and c=3.

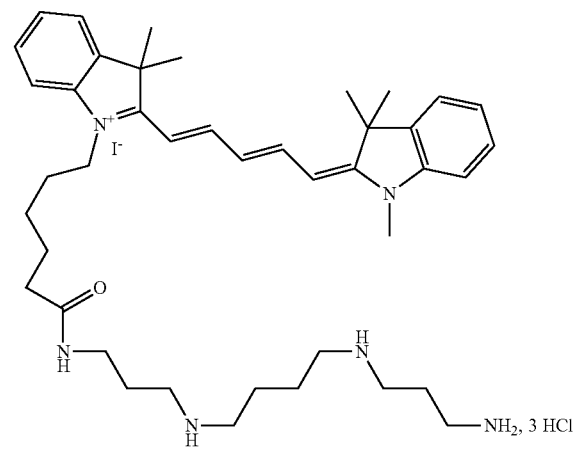 [SMILES: CN1/C(=C/C=C/C=C/C2=[N+](CCCCCC(=O)NCCCNCCCCNCCCN)c3ccccc3C2(C)C)C(C)(C)c2ccccc21 ; [I-]]

0.5 g of the preparation from stage 2 of this example in solution in 65 mL of 3:1 dichloromethane/ethanol mixture is left in contact for 1 hour under stirring at ambient temperature in the presence of 2 mL of a 4M HCl/dioxane solution. The solvent is evaporated at reduced pressure to obtain a deep blue residue in trihydrochloride form. Purification is performed by means of preparative HPLC on a Sunfire C-18 5μ, 19×250 mm column, λ: 220 nm, flow rate: 20 mL/min. Mobile phase gradient: 100% 5 mM HCl to 85% 5 mM HCl—15% acetonitrile. The fractions in question are freeze-dried after removing the acetonitrile at reduced pressure. The freeze-dried product is taken up with a 1:1 dichloromethane/isopropyl ether mixture, filtered and vacuum-dried to obtain 130 mg of deep blue solid. (Yd=29.4%).

$C_{42}H_{63}IN_6O$, 3HCl: 857.314—(Mass ESI+180° C. M=667.6).

Analytical HPLC purity: 96.7% C8-X-bridge 5 micron 4.6×250 mm column. λ: 220 nm—mobile phase 60% 6.8 g/L pH 4 $KH_2PO_4$ buffer—40% $CH_3CN$. Retention time: 7.37 min.

$SiO_2$ TLC: 90/10/1 $CH_2Cl_2$/Methanol/$NH_4OH$+ammonia vessel—Rf: 0.15.

$^1$H NMR (500 MHz, DMSO-d6) δ=9.25 (2H, br. s., H-15"), 9.09 (2H, br. s., H-10"), 8.34 (2H, t, J=13.0 Hz, H-14', 14), 8.15 (4H, br. s., H-19'''), 8.09 (1H, t, J=5.6 Hz, H-6"), 7.61 (2H, d, J=7.3 Hz, H-6', 6), 7.39 (4H, d, J=2.4 Hz, H-4', 4, 3', 3), 7.20-7.29 (2H, m, H-5', 5), 6.58 (1H, t, J=12.4 Hz, H-15'), 6.32 (1H, d, J=13.7 Hz, H-13), 6.28 (1H, d, J=14.0 Hz, H-13'), 4.09 (2H, t, J=7.2 Hz, H-10'), 3.60 (3H, s, H-10), 3.09 (2H, q, J=6.6 Hz, H-7"), 2.93-3.02 (2H, m, H-16"), 2.88 (8H, s, H-14", 11", 9", 18"), 2.08 (2H, t, J=7.3 Hz, H-4"), 1.99 (2H, quin, J=7.4 Hz, H-17"), 1.74-1.82 (2H, m, H-8″), 1.68 (12H, s, H-11, 12, 11′, 12′), 1.71 (6H, s, H-1″, 13″, 12″), 1.48-1.60 (21-1, m, H-3″), 1.29-1.42 (2H, m, H-2″)

$^{13}$C NMR (126 MHz, DMSO-d6) δ=173.3 (C-9), 172.5 (C-9′), 172.3 (C-5″), 154.1 (C-14′, 14), 142.8 (C-2), 142.1 (C-2′), 141.1 (C-7), 141.1 (C-7′), 128.5 (C-4), 128.4 (C-4′), 125.4 (C-15′), 124.8 (C-5), 124.7 (C-5′), 122.5 (C-6′), 122.4 (C-6), 111.1 (C-3, 3′), 103.4 (C-13), 103.1 (C-13′), 48.9 (C-8′, 8), 46.0 (C-14″, 11″), 44.6 (C-9″), 43.8 (C-16″), 43.3 (C-10′), 39.9, 39.8, 39.6, 36.2 (C-18″), 35.7 (C-7″), 35.2 (C-4″), 31.2 (C-10), 27.2 (C-12′, 12), 27.0 (C-11′, 11), 26.8 (C-1″), 25.9 (C-8″), 25.8 (C-2″), 25.0 (C-3″), 23.6 (C-17″), 22.6 (C-12″), 22.6 (C-13″).

As in example 2, but using the corresponding starting materials (*J. Org. Chem.* 2004, 69, 3530; *Synthesis* 2002, 2195; *Synthesis* 1994, 37; *J. Org. Chem.* 1978, 44, 1166), the products in examples 3 to 5 are prepared.

Example 3

1-{5-[3-(4-aminobutylamino)-propylcarbamoyl]-pentyl}-3,3-dimethyl-2-{(1E,3E)-5-[1,3,3-trimethyl-1,3-dihydroindol-(2E)-ylidene]-penta-1,3-dienyl}-3H-indolium iodide Compound having formula (I) where R1=R2=H, R3=Me, X=I, n=1, m=5, d=0, e=1, b=3, and c=4.

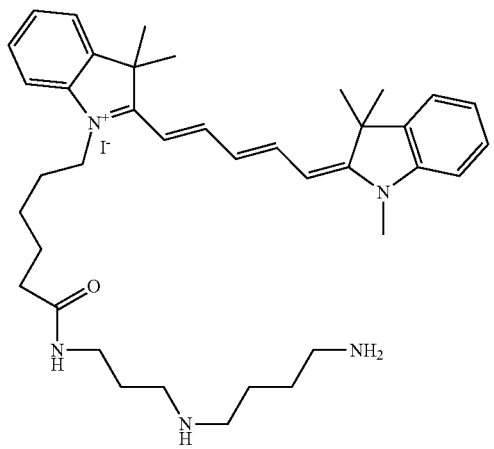 [SMILES: CN1/C(=C/C=C/C=C/C2=[N+](CCCCCC(=O)NCCCNCCCCN)c3ccccc3C2(C)C)C(C)(C)c2ccccc21 ; [I-]]

$C_{39}H_{56}N_5OI=737.81$.

Example 4

1-{5-[4-(3-aminopropylamino)-butylcarbamoyl]-pentyl}-3,3-dimethyl-2-{(1E,3E)-5-[1,3,3-trimethyl-1,3-dihydroindol-(2E)-ylidene]-penta-1,3-dienyl}-3H-indolium iodide Compound having formula (I) where R1=R2=H, R3=Me, X=I, n=1, m=5, d=0, e=1, b=4, and c=3.

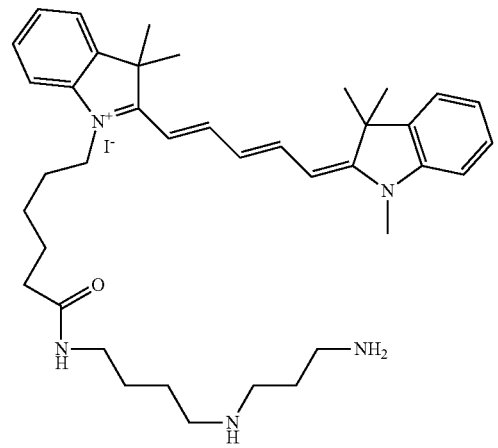 [SMILES: CN1/C(=C/C=C/C=C/C2=[N+](CCCCCC(=O)NCCCCNCCCN)c3ccccc3C2(C)C)C(C)(C)c2ccccc21 ; [I-]]

$C_{39}H_{56}N_5OI=737.81$.

Example 5

1-{5-[4-amino-butylcarbamoyl]-pentyl}-3,3-dimethyl-2-{(1E,3E)-5-[1,3,3-trimethyl-1,3-dihydroindol-(2E)-ylidene]-penta-1,3-dienyl}-3H-indolium iodide Compound having formula (I) where R1=R2=H, R3=Me, X=I, n=1, m=5, d=1, a=4, and e=0)

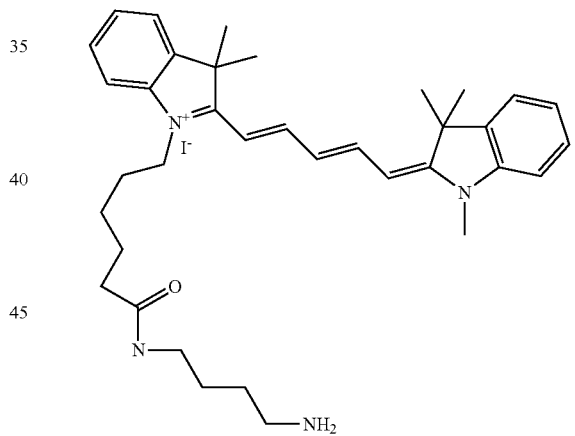

$C_{36}H_{49}N_4OI=680.72$.

As in example 1, but using the corresponding starting materials (*J. Org. Chem.* 2004, 69, 3530; *Synthesis* 2002, 2195; Synthesis 1994, 37; *J. Org. Chem.* 1978, 44, 1166), the product in example 6 is prepared.

Example 6

1-{5-[4-(3-aminopropylamino)-butylcarbamoyl]-pentyl}-3,3-dimethyl-2-{(1E,3E)-5-[1-butyl-3,3-dimethyl-1,3-dihydroindol-(2E)-ylidene]-penta-1,3-dienyl}-3H-indolium bromide Compound having formula (I) where R1=R2=H, R3=Me, X=I, n=1, m=5, d=0, e=1, b=4, and c=3.

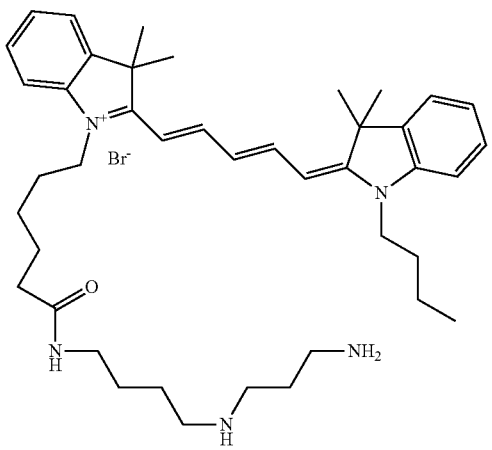 [SMILES: CCCCN1/C(=C/C=C/C=C/C2=[N+](CCCCCC(=O)NCCCCNCCCN)c3ccccc3C2(C)C)C(C)(C)c2ccccc21 ; [Br-]]

$C_{42}H_{62}BrN_5O=732.90$.

Example 7

1-(5-{3-[4-(3-aminopropylamino)butylamino]-propylcarbamoyl}-pentyl)-2-{(1E,3E,5E)-7-[1-butyl-3,3-dimethyl-1,3-dihydroindol-(2E)-ylidene]-hepta-1,3,5-trienyl}-3,3-dimethyl-3H-indolium bromide Compound having formula (I) where R1=R2=H, R3=nBu, X=Br, n=3, m=5, d=e=1, a=3, b=4, and c=3.

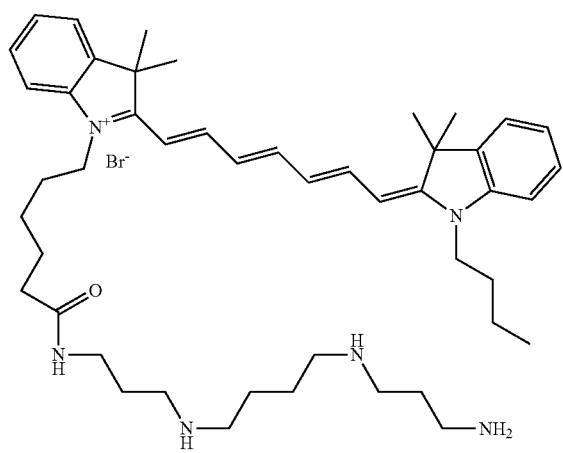 [SMILES: CCCCN1/C(=C/C=C/C=C/C=C/C2=[N+](CCCCCC(=O)NCCCNCCCCNCCCN)c3ccccc3C2(C)C)C(C)(C)c2ccccc21 ; [Br-]]

Stage 1—

Preparation of 1-butyl-3,3-dimethyl-2-((1E,3E,5E)-6-(N-phenylacetamido)hexa-1,3,5-trienyl)-3H-indolium bromide. Compound having formula (VII) where R2=H, R3=nBu, n=3, and X=Br.

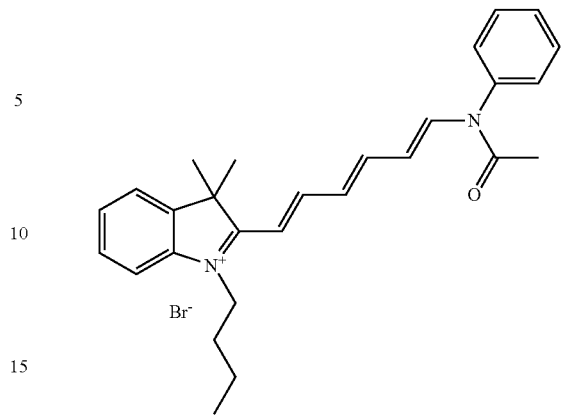

A mixture of 3 g of the preparation from stage 4 of example 1, with 5.7 g of glutacondianyl hydrochloride in solution in 45 mL of 2:1 acetic anhydride and acetic acid mixture is heated to reflux for 2 hours. The solvent is evaporated at reduced pressure and the residue obtained is fixed on silica for purification by flash chromatography (gradient on silica: 100% ethyl acetate to 90:10 ethyl acetate/methanol). The fractions in question are evaporated to obtain 2.6 g of scarab red oil (Yd=52%).

$C_{28}H_{33}BrN_2O$: 493.49 (mass APCI+500° C. $MH^+=413.2$).

Stage 2—

Preparation of 1-(9,14-bis(tert-butoxycarbonyl)-2,2-dimethyl-4,19-dioxo-3-oxa-5,9,14,18-tetraazatetracosan-24-yl)-2-((1E,3E,5E,7E)-7-(1-butyl-3,3-dimethylindolin-2-ylidene)hepta-1,3,5-trienyl)-3,3-dimethyl-3H-indolium bromide. Compound having formula (VIII) where R1=R2=H, R3=nBu, X=Br, n=3, and m=5, the protected polyamine consists of the compound having formula (IX) where P=COOtBu, d=e=1, a=3, b=4, and c=3.

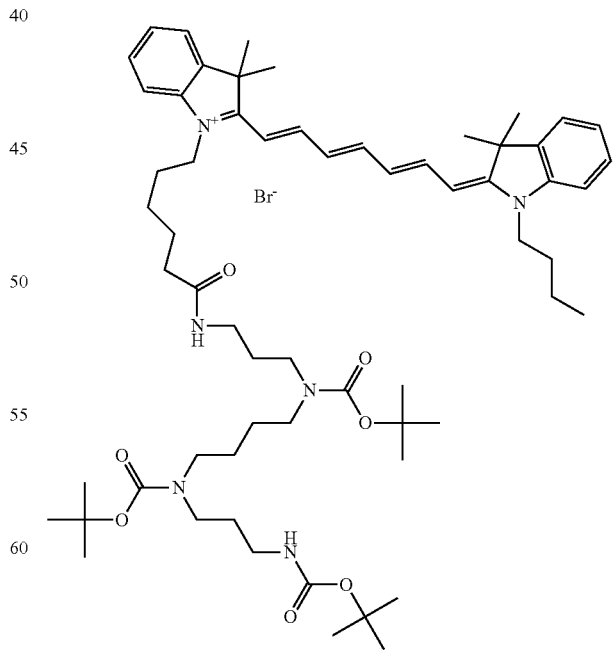

A mixture of 1.2 g of the preparation from stage 3 of example 1 and 4.2 g of the preparation from stage 1 above in this example, in solution in 50 mL of ethanol in the presence of 1.2 g of sodium acetate is left under stirring at ambient temperature for approximately 2 hours. After adding silica, the product is fixed thereon by evaporating ethanol at reduced pressure. The product is purified by $SiO_2$ flash chromatography (gradient: 100% ethyl acetate to 75% ethyl acetate—25% methanol). The fractions in question are evaporated at reduced pressure to obtain 1.28 g of scarab green solid (Yd=46.2%).

$C_{62}H_{95}BrN_6O_7$: 1116.39 (mass APCI+500° C. M=1035.6).

Stage 3—

Preparation of, 1-(5-{3-[4-(3-aminopropylamino)butylamino]-propylcarbamoyl}-pentyl)-2-{(1E,3E,5E)-7-[1-butyl-3,3-dimethyl-1,3-dihydroindol-(2E)-ylidene]-hepta-1,3,5-trienyl}-3,3-dimethyl-3H-indolium bromide trihydrochloride. Compound having formula (I) R1=R2=H, R3=nBu, X=Br, n=3, m=5, d=e=1, a=3, b=4, and c=3.

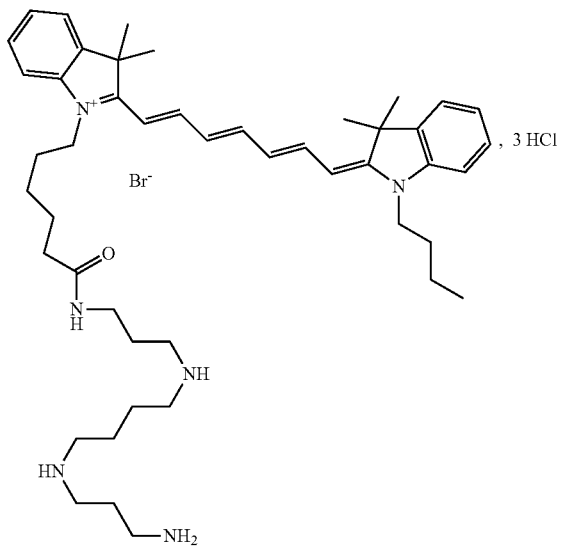 [SMILES: CCCCN1/C(=C/C=C/C=C/C=C/C2=[N+](CCCCCC(=O)NCCCNCCCCNCCCN)c3ccccc3C2(C)C)C(C)(C)c2ccccc21 ; [Br-]]

1.2 g of the preparation from stage 2 above of this example, in solution in 100 mL of dichloromethane is left in contact for 2 hours under stirring at ambient temperature in the presence of 10 mL of a 4M HCl/dioxane solution. The solvent is evaporated at reduced pressure to obtain a deep green residue which is crystallised in ethyl acetate. After filtration and drying, 0.95 g of a deep green solid of the product in the trihydrochloride form thereof is obtained (Yd=29.4%).

$C_{47}H_{71}BrN_6O$, 3HCl: 925.43—(Mass ESI+400° C.: MH/2=368.4 and M=607.5).

Analytical HPLC purity: 97.4% C8-X-bridge 5 micron 4.6×250 mm column. λ: 750 nm—mobile phase 60% 6.8 g/L pH 4 $KH_2PO_4$ buffer—40% $CH_3CN$. Retention time: 12.15 min.

As in example 7 but using the corresponding starting materials, the products in examples 8 to 11 are prepared.

Example 8

1-(5-{3-[4-(3-aminopropylamino)butylamino]-propylcarbamoyl}-pentyl)-2-{(1E,3E,5E)-7-[1,3,3-trimethyl-1,3-dihydroindol-(2E)-ylidene]-hepta-1,3,5-trienyl}-3,3-dimethyl-3H-indolium iodide Compound having formula (I) where R1=R2=H, R3=Me, X=I, n=3, m=5, d=e=1, a=3, b=4, and c=3.

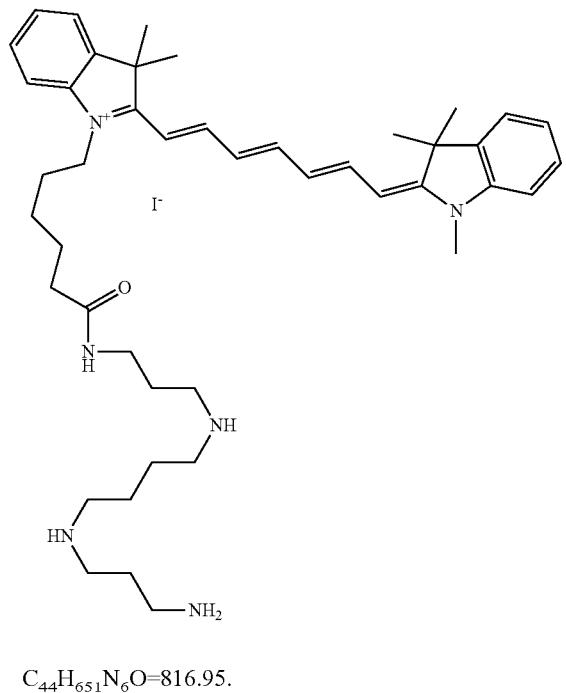

$C_{44}H_{651}N_6O$=816.95.

Example 9

1-{5-[4-(3-aminopropylamino)-butylcarbamoyl]-pentyl}-3,3-dimethyl-2-{(1E,3E,5E)-7-[1,3,3-trimethyl-1,3-dihydroindol-(2E)-ylidene]-hepta-1,3,5-trienyl}-3H-indolium iodide Compound having formula (I) where R1=R2=H, R3=Me, X=I, n=3, m=5, d=0, e=1, b=4, and c=3.

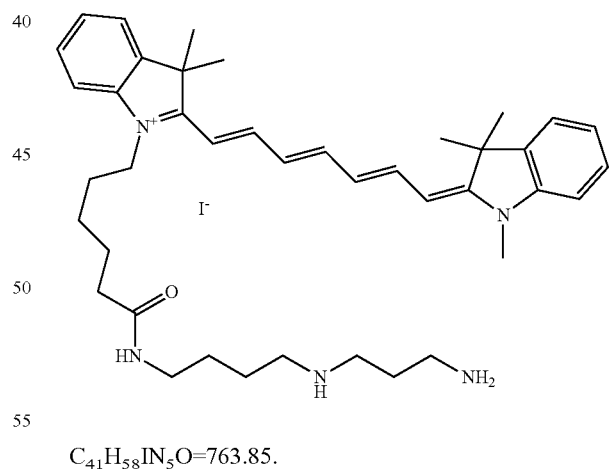

$C_{41}H_{58}IN_5O$=763.85.

Example 10

1-{5-[3-(4-aminobutylamino)-propylcarbamoyl]-pentyl}-3,3-dimethyl-2-{(1E,3E,5E)-7-[1,3,3-trimethyl-1,3-dihydroindol-(2E)-ylidene]-hepta-1,3,5-trienyl}-3H-indolium iodide Compound having formula (I) where R1=R2=H, R3=Me, X=I, n=3, m=5, d=0, e=1, b=3, and c=4.

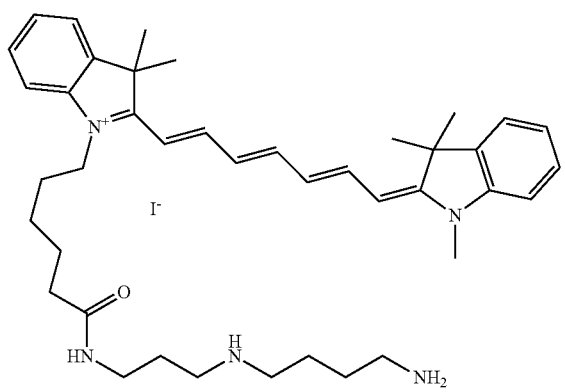 [SMILES: CN1/C(=C/C=C/C=C/C=C/C2=[N+](CCCCCC(=O)NCCCNCCCCN)c3ccccc3C2(C)C)C(C)(C)c2ccccc21 ; [I-]]

$C_{41}H_{58}IN_5O = 763.85.$

Example 11

1-[5-(4-aminobutylamino)-pentyl]-3,3-dimethyl-2-{(1E,3E,5E)-7-[1,3,3-trimethyl-1,3-dihydroindol-(2E)-ylidene]-hepta-1,3,5-trienyl}-3H-indolium iodide Compound having formula (I) where R1=R2=H, R3=Me, X=I, n=3, m=5, d=1, a=1, and e=0.

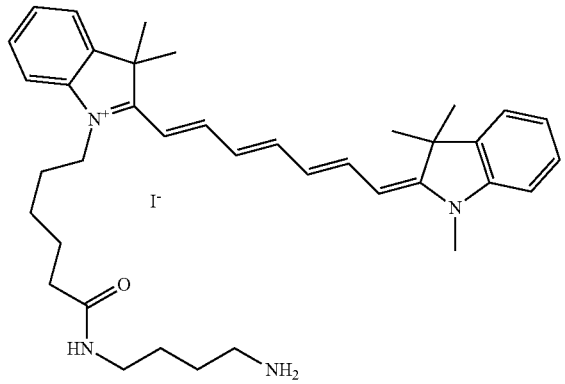 [SMILES: CN1/C(=C/C=C/C=C/C=C/C2=[N+](CCCCCC(=O)NCCCCN)c3ccccc3C2(C)C)C(C)(C)c2ccccc21 ; [I-]]

$C_{38}H_{51}IN_4O = 706.76.$

II—Pharmacological Study

For the majority of anticancer therapies currently used in clinical practice, there is no biomarker suitable for identifying tumours which are likely to respond to the proposed therapy. The present invention relates to fluorescent cyanine-polyamine derivatives for use as diagnostic probes for selecting tumours eligible for treatment with an anticancer compound vectorised by the polyamine transport system. Unlike the probes claimed in the patent WO 2009/013360 emitting a fluorescence having wavelengths λ~450-520 nm, the present invention relates to probes which are fluorescent in the near infrared range (λ~650-900 nm), i.e. in the spectral window suitable for in vivo detection by means of fluorescence imaging. Indeed, the fluorescence of wavelengths λ~450-520 nm is difficult to detect in vivo since it is mostly absorbed by tissues. Such probes are thus necessarily used in vitro and the application thereof to tumour diagnostics thus requires a tumour biopsy procedure. On the other hand, the cyanine probes according to the present invention (λ~650-900 nm) are directly applicable in vivo when administered to small animals and could be applicable to humans, followed by gaseous anaesthesia of the animal/patient, and using the suitable detection apparatus, the fluorescence emission by the probe accumulating in the tumour being recorded over time. The probes according to the present invention are thus suitable for conducting a direct examination of the subject's tumour, non-invasively. They could also be suitable for monitoring the therapeutic response over time.

Example 12

In Vivo Detection of the Fluorescence Emitted by the Cyanine Polyamine Probe 7-7 of Example 7 Accumulating in a Tumour on an Animal Method 1_Animals 6 healthy male C57B16 mice, aged 11 weeks, were used to evaluate the tolerance of the injection of increasing doses of the probe of example 7 (F98942) (25, 50 and 100 µg). 11 male C57B16 mice aged 10 weeks were grafted subcutaneously on the right rear paw with $2.5 \cdot 10^5$ B16/F10-Luc mouse melanoma cells.

2_Probe

The probe F98942 is placed in solution in sterile 5% glucose serum extemporaneously.

3_Fluorescence Imaging

The mice were injected with 50 µg or 25 µg of F98942 or PBS (Phosphate Buffered Saline) intravenously. They were then anaesthetised by isoflurane gas inhalation (3% isoflurane/oxygen) prior to the fluorescence imaging examination 24 and 48 hours post-injection. After 48 hours, the tumours were removed and analysed by means of fluorescence imaging.

Results

Injecting the probe in healthy mice was well-tolerated regardless of the dose. The fluorescence of the probe F98942 is detected in the tumour B16F10 in vivo as shown in the following table and in FIG. 1.

| | | Tumour fixation | |
|---|---|---|---|
| | | Fluorescence at t = 24 hrs | Mean |
| Mouse | F98942 (µg) | [p/s/cm²/sr]/[µW/cm²] | [p/s/cm²/sr]/[µW/cm²] |
| 1 | 50 | $3.22 \cdot 10^7$ | $3.14 \cdot 10^7$ |
| 2 | 50 | $3.08 \cdot 10^7$ | |
| 3 | 50 | $3.12 \cdot 10^7$ | |
| 4 | 50 | $3.01 \cdot 10^7$ | |
| 5 | 25 | $2.10 \cdot 10^7$ | $1.81 \cdot 10^7$ |
| 6 | 25 | $1.52 \cdot 10^7$ | |
| 7 | 0 | $1.01 \cdot 10^6$ | $1.02 \cdot 10^6$ |
| 8 | 0 | $1.02 \cdot 10^6$ | |

Example 13 (Comparative)

In Vivo Detection of Fluorescence Emitted by the Following Comparative Probe

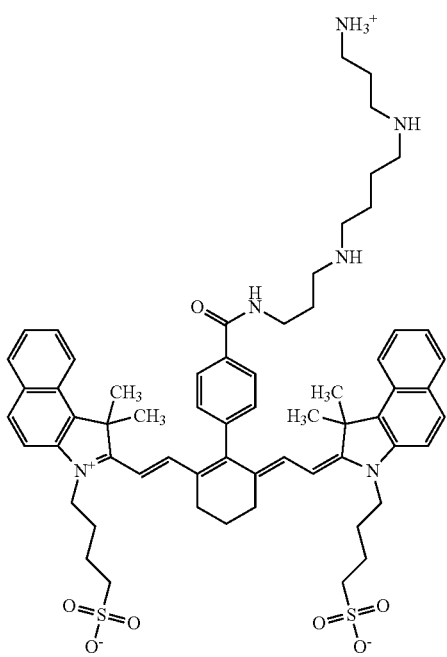 [SMILES: CC1(C)C(/C=C/C2=C(c3ccc(C(=O)NCCCNCCCCNCCC[NH3+])cc3)C(=C/C=C3/N(CCCCS(=O)(=O)[O-])c4ccc5ccccc5c4C3(C)C)/CCC2)=[N+](CCCCS(=O)(=O)[O-])c2ccc3ccccc3c21]

The same test as that in example 12 was conducted with the comparative probe described above. However, this compound was not detected since the fluorescence level thereof was too low.

The invention claimed is:

1. A compound having the following formula (I):

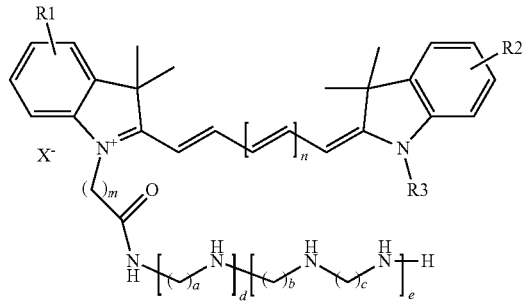

wherein:

R1, R2, R3, n, m, a, b, c, d, e and X are defined such that the compound of formula (I) is chosen from:

1) 1-(6-(3-(4-(3-aminopropylamino)butylamino)propylamino)-6-oxohexyl) 2-((1E,3E,5E)-5-(1-methyl-3,3-dimethylindolin-2-ylidene)penta-1,3-dienyl)-3,3-dimethyl-3H-indolium iodide,
2) 1-{5-[4-(3-aminopropylamino)-butylcarbamoyl]-pentyl}-3,3-dimethyl-2-{(1E,3E)-5-[1,3,3-trimethyl-1,3-dihydroindol-(2E)-ylidene]-penta-1,3-dienyl}-3H-indolium iodide,
3) 1-{5-[3-(4-aminobutylamino)-propylcarbamoyl]-pentyl}-3,3-dimethyl-2-{(1E,3E)-5-[1,3,3-trimethyl-1,3-dihydroindol-(2E)-ylidene]-penta-1,3-dienyl}-3H-indolium iodide,
4) 1-{5-[4-amino-butylcarbamoyl]-pentyl}-3,3-dimethyl-2-{(1E,3E)-5-[1,3,3-trimethyl-1,3-dihydroindol-(2E)-ylidene]-penta-1,3-dienyl}-3H-indolium iodide,
5) 1-(6-(3-(4-(3-aminopropylamino)butylamino)propylamino)-6-oxohexyl)2-((1E,3E,5E)-5-(1-butyl-3,3-dimethylindolin-2-ylidene)penta-1,3-dienyl)-3,3-dimethyl-3H-indolium bromide,
6) 1-{5-[4-(3-aminopropylamino)-butylcarbamoyl]-pentyl}-3,3-dimethyl-2-{(1E,3E)-5-[1-butyl-3,3-dimethyl-1,3-dihydroindol-(2E)-ylidene]-penta-1,3-dienyl}-3H-indolium bromide,
7) 1-(5-{3-[4-(3-aminopropylamino)butylamino]-propylcarbamoyl}-pentyl)-2-{(1E,3E,5E)-7-[1,3,3-trimethyl-1,3-dihydroindol-(2E)-ylidene]-hepta-1,3,5-trienyl}-3,3-dimethyl-3H-indolium iodide,
8) 1-{5-[4-(3-aminopropylamino)-butylcarbamoyl]-pentyl}-3,3-dimethyl-2-{(1E,3E,5E)-7-[1,3,3-trimethyl-1,3-dihydroindol-(2E)-ylidene]-hepta-1,3,5-trienyl}-3H-indolium iodide,
9) 1-{5-[3-(4-aminobutylamino)-propylcarbamoyl]-pentyl}-3,3-dimethyl-2-{(1E,3E,5E)-7-[1,3,3-trimethyl-1,3-dihydroindol-(2E)-ylidene]-hepta-1,3,5-trienyl}-3H-indolium iodide,
10) 1-[5-(4-aminobutylamino)-pentyl]-3,3-dimethyl-2-{(1E,3E,5E)-7-[1,3,3-trimethyl-1,3-dihydroindol-(2E)-ylidene]-hepta-1,3,5-trienyl}-3H-indolium iodide,
11) 1-(5-{3-[4-(3-aminopropylamino)butylamino]-propylcarbamoyl}-pentyl)-2-{(1E,3E,5E)-7-[1-butyl-3,3-dimethyl-1,3-dihydroindol-(2E)-ylidene]-hepta-1,3,5-trienyl}-3,3-dimethyl-3H-indolium bromide,
12) 1-{5-[4-(3-aminopropylamino)-butylcarbamoyl]-pentyl}-3,3-dimethyl-2-{(1E,3E,5E)-7-[1-butyl-3,3-dimethyl-1,3-dihydroindol-(2E)-ylidene]-hepta-1,3,5-trienyl}-3H-indolium bromide,
13) 1-{5-[3-(4-aminobutylamino)-propylcarbamoyl]-pentyl}-3,3-dimethyl-2-{(1E,3E,5E)-7-[1-butyl-3,3-dimethyl-1,3-dihydroindol-(2E)-ylidene]-hepta-1,3,5-trienyl}-3H-indolium bromide, and
14) 1-[5-(4-aminobutylcarbamoyl)-pentyl]-2-{(1E,3E,5E)-7-[1-butyl-3,3-dimethyl-1,3-dihydroindol-(2E)-ylidene]-hepta-1,3,5-trienyl}-3,3-dimethyl-3H-indolium bromide, or a pharmaceutically acceptable salt thereof.

2. The compound according to claim 1, wherein the pharmaceutically acceptable salt is a hydrochloric acid addition salt.

3. A diagnostic composition comprising at least one compound having formula (I) according to claim 1, or a pharmaceutically acceptable salt thereof and at least one pharmaceutically acceptable excipient.

4. A process for synthesising a compound having formula (I) according to claim 1, or a pharmaceutically acceptable salt thereof comprising the following successive steps:

(i) coupling between a compound having the following formula (VII):

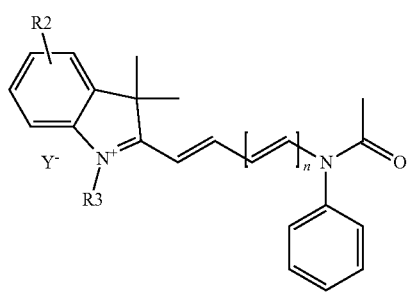

(VII)

wherein R2, R3, and n are as defined in claim 1 and Y represents a halogen atom,
with a compound having the following formula (V):

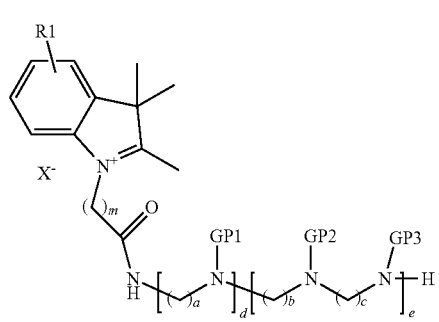

(V)

wherein:
R1, m, a, b, c, d, e, and X are as defined in claim 1 and GP1, GP2 and GP3, identical or different, represent an N-protecting group, to obtain a compound having the following formula (VIII):

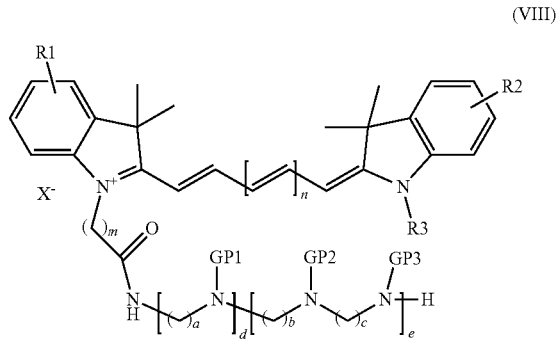

(VIII)

wherein, R1, R2, R3, X, m, n, a, b, c, d, e, GP1, GP2 and GP3 are as defined above,
(ii) deprotecting the amine functions protected by the GP1, GP2 and GP3 groups in the compound having formula (VIII) obtained in step (i) above to obtain a compound having formula (I) according to claim 1,
(iii) optionally salifying the compound having formula (I) obtained in step (ii) above to obtain a pharmaceutically acceptable salt thereof, and
(iv) separating the compound having formula (I) or the pharmaceutically acceptable salt thereof obtained in the previous step from the reaction medium.

5. The process according to claim 4, wherein step (i) is carried out in the presence of sodium acetate.

6. The process according to claim 4, wherein the compound having formula (V) is obtained by peptide coupling between a compound having the following formula (III):

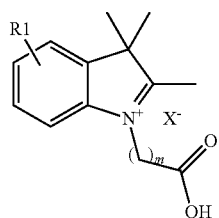

(III)

wherein R1, m and X are as defined in claim 4,
with a protected polyamine having the following formula (IX):

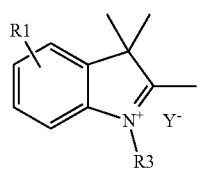

(IX)

wherein a, b, c, d, e, GP1, GP2 and GP3 are as defined in claim 4, or an acid addition salt thereof.

7. The process according to claim 4, wherein the compound having formula (VII) is obtained by coupling between a compound having the following formula (IV):

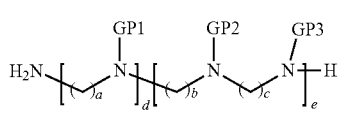

(IV)

wherein R2, R3 and Y are as defined in claim 4,
and a compound having the following formula (VI):

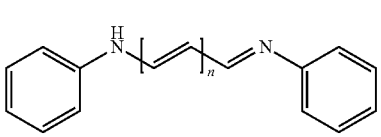

(VI)

wherein n is as defined in claim 4, or an acid addition salt thereof.

8. The process according to claim 5, wherein step (i) is carried out in ethanol as solvent.

9. A method for detecting in vivo a cancer tumour expressing the polyamine transport system comprising administering an effective amount of a compound having formula (I) according to claim 1 or a pharmaceutically acceptable salt thereof to a person in need thereof; and detecting the fluorescence emitted by the compound having formula (I) by fluorescence medical imaging.

10. A method for detecting in vitro a cancer tumour expressing the polyamine transport system comprising administering an effective amount of a compound having formula (I) according to claim 1 or a pharmaceutically acceptable salt thereof in vitro; and detecting the fluorescence emitted by the compound having formula (I).

* * * * *

UNITED STATES PATENT AND TRADEMARK OFFICE
CERTIFICATE OF CORRECTION

PATENT NO. : 9,439,982 B2
APPLICATION NO. : 13/822535
DATED : September 13, 2016
INVENTOR(S) : Yves Guminski et al.

It is certified that error appears in the above-identified patent and that said Letters Patent is hereby corrected as shown below:

In the Specification

At Column 11, in Compound III, replace 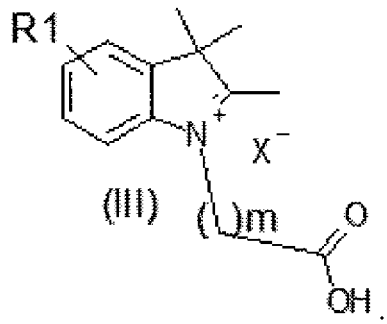 with 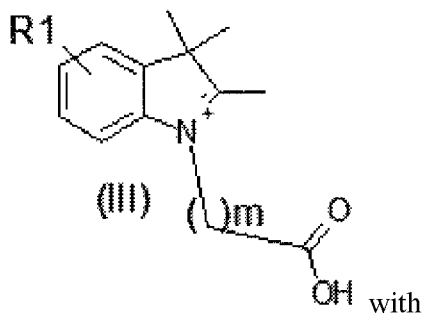

Signed and Sealed this
Third Day of October, 2017

Joseph Matal
*Performing the Functions and Duties of the*
*Under Secretary of Commerce for Intellectual Property and*
*Director of the United States Patent and Trademark Office*

At Column 15, Line 17, replace 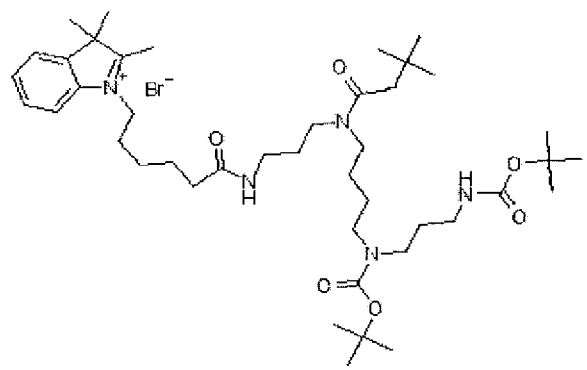 with 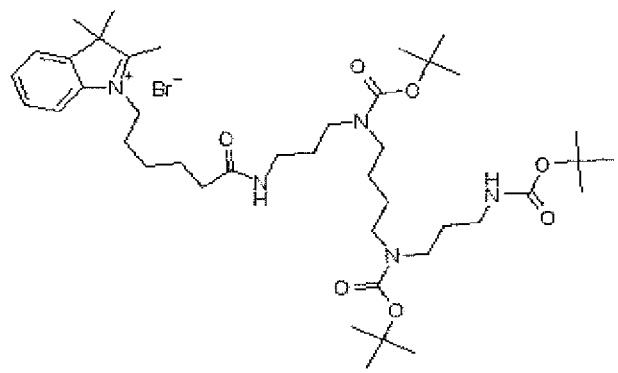
In the Claims
In Claim 7, at Column 32, Line 31, in Formula (IV), replace 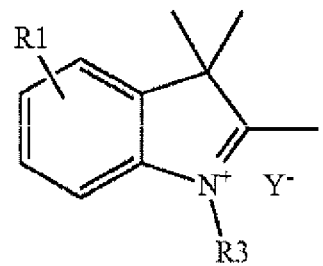 with 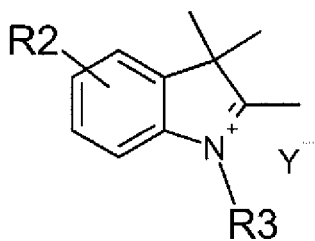 .